(12) United States Patent
Bajaj

US011531021B2

(10) Patent No.: US 11,531,021 B2
(45) Date of Patent: Dec. 20, 2022

(54) MEASURING AND REMOVING NOISE IN STOCHASTIC SIGNALS FROM A NANOPORE DNA SEQUENCING SYSTEM DRIVEN BY AN ALTERNATING SIGNAL

(71) Applicant: Roche Sequencing Solutions, Inc., Pleasanton, CA (US)

(72) Inventor: Kapil M. S. Bajaj, Newark, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/946,534

(22) Filed: Jun. 25, 2020

(65) Prior Publication Data

US 2021/0018486 A1    Jan. 21, 2021

Related U.S. Application Data

(63) Continuation of application No. PCT/EP2018/085734, filed on Dec. 19, 2018.

(60) Provisional application No. 62/610,932, filed on Dec. 28, 2017.

(51) Int. Cl.
*G01N 33/487* (2006.01)
*C12Q 1/6869* (2018.01)
*G01N 27/40* (2006.01)

(52) U.S. Cl.
CPC .   *G01N 33/48721* (2013.01); *G01N 33/48728* (2013.01); *C12Q 1/6869* (2013.01); *G01N 27/40* (2013.01)

(58) Field of Classification Search
None
See application file for complete search history.

(56) References Cited

U.S. PATENT DOCUMENTS

| | | | |
|---|---|---|---|
| 5,733,729 A | 3/1998 | Lipshutz et al. |
| 5,853,979 A | 12/1998 | Green et al. |
| 6,066,454 A | 5/2000 | Lipshutz et al. |
| 6,228,593 B1 | 5/2001 | Lipshutz et al. |
| 6,546,340 B2 | 4/2003 | Lipshutz et al. |
| 6,957,149 B2 | 10/2005 | Lipshutz et al. |
| 7,039,238 B2 | 5/2006 | Sonmez et al. |
| 7,133,781 B2 | 11/2006 | Toll et al. |
| 7,617,054 B2 | 11/2009 | Sayer et al. |
| 8,126,235 B2 | 2/2012 | Shi et al. |
| 8,182,993 B2 | 5/2012 | Tomaney et al. |
| 8,200,648 B2 | 6/2012 | Boiman et al. |
| 8,370,079 B2 | 2/2013 | Sorenson et al. |
| 8,428,886 B2 | 4/2013 | Wong et al. |
| 8,645,343 B2 | 2/2014 | Wong et al. |
| 8,703,422 B2 | 4/2014 | Tomaney et al. |
| 9,165,109 B2 | 10/2015 | Chaisson |
| 9,175,343 B2 | 11/2015 | Tomaney et al. |
| 9,194,838 B2 | 11/2015 | Taniguchi et al. |
| 9,218,451 B2 | 12/2015 | Wong et al. |
| 9,395,353 B2 | 7/2016 | Gu et al. |
| 9,546,400 B2 | 1/2017 | Turner et al. |
| 9,574,228 B2 | 2/2017 | Gu et al. |
| 2009/0012766 A1 | 1/2009 | Miyake et al. |
| 2010/0122907 A1 | 5/2010 | Stanford et al. |
| 2012/0173159 A1 | 7/2012 | Davey et al. |
| 2013/0060482 A1 | 3/2013 | Sikora et al. |
| 2013/0090860 A1 | 4/2013 | Sikora et al. |
| 2013/0146456 A1 | 6/2013 | Gundlach et al. |
| 2013/0217006 A1 | 8/2013 | Sorenson et al. |
| 2013/0274148 A1 | 10/2013 | Kain et al. |
| 2014/0051068 A1 | 2/2014 | Cherf et al. |
| 2014/0134616 A1 | 5/2014 | Davis et al. |
| 2015/0060276 A1 | 3/2015 | Golovchenko et al. |
| 2015/0107996 A1 | 4/2015 | Chen |
| 2015/0111759 A1 | 4/2015 | Ju et al. |
| 2015/0119259 A1* | 4/2015 | Ju .................. C12Q 1/6869 506/2 |
| 2015/0169824 A1 | 6/2015 | Kermani et al. |
| 2015/0193431 A1 | 7/2015 | Stoytchev et al. |
| 2015/0344945 A1 | 12/2015 | Mandell et al. |
| 2016/0097093 A1 | 4/2016 | Tomaney et al. |
| 2016/0110499 A1 | 4/2016 | Donnet |
| 2016/0138101 A1 | 5/2016 | Taniguchi et al. |
| 2016/0162634 A1 | 6/2016 | Reid et al. |
| 2017/0002403 A1 | 1/2017 | Gu et al. |
| 2017/0089858 A1 | 3/2017 | Fernandez-Gomez et al. |
| 2017/0091427 A1 | 3/2017 | Massingham |
| 2017/0096703 A1 | 4/2017 | Dolan et al. |
| 2017/0154036 A9 | 6/2017 | Stoytchev et al. |
| 2017/0219557 A1 | 8/2017 | Reid et al. |

FOREIGN PATENT DOCUMENTS

| | | |
|---|---|---|
| CN | 102834527 A | 12/2012 |
| CN | 102899243 A | 1/2013 |
| CN | 103392008 A | 11/2013 |
| CN | 104066850 A | 9/2014 |
| CN | 102621214 B | 10/2014 |
| EP | 0835442 B1 | 3/1999 |
| EP | 104955958 A | 9/2015 |
| EP | 2758545 | 7/2017 |

(Continued)

OTHER PUBLICATIONS

International Search Report and Written Opinion dated Apr. 18, 2019 in connection with PCT/EP2018/085734 filed Dec. 19, 2018, pp. 1-13.

(Continued)

*Primary Examiner* — G Steven Vanni
(74) *Attorney, Agent, or Firm* — Winston Chu

(57) ABSTRACT

A method of using a sequencing cell includes applying an alternating signal across a nanopore of the sequencing cell. The method further includes acquiring a first set of voltage data during a first portion of a plurality of cycles of the alternating signal. The method further includes determining a shifted set of voltage data from the first set of voltage data, computing difference data values by computing differences between data points of the first set of voltage data and corresponding data points of the shifted set of voltage data, identifying a plurality of noise data points as data points having difference data values that are larger than a first threshold value, and removing the plurality of noise data points from the first set of voltage data.

13 Claims, 17 Drawing Sheets

(56) References Cited

FOREIGN PATENT DOCUMENTS

| | | | |
|---|---|---|---|
| JP | 58223927 | A | 12/1983 |
| JP | 2003531592 | A | 10/2003 |
| JP | 2010501077 | A | 1/2010 |
| JP | 2010066012 | A | 3/2010 |
| JP | 2010524436 | A | 7/2010 |
| JP | 2010256268 | A | 11/2010 |
| JP | 2014174022 | A | 9/2014 |
| JP | 2016095314 | A | 5/2016 |
| JP | 2017534889 | A | 11/2017 |
| WO | 0181908 | A1 | 11/2001 |
| WO | 2008021488 | A1 | 2/2008 |
| WO | 2008124107 | A1 | 10/2008 |
| WO | 2011097028 | A1 | 8/2011 |
| WO | 2013041878 | A1 | 3/2013 |
| WO | 2016023010 | A1 | 2/2016 |
| WO | 2016073318 | A1 | 5/2016 |

OTHER PUBLICATIONS

Wang et al., The evolution of nanopore sequencing, Frontiers in Genetics, Jan. 7, 2015, (20 pp.), vol. 5, Art. 449.
International Search Report and Written Opinion dated Aug. 30, 2017 in corresponding PCT/EP2017/065423, pp. 1-11.

\* cited by examiner

MEASURING AND REMOVING NOISE IN STOCHASTIC SIGNALS FROM A NANOPORE DNA SEQUENCING SYSTEM DRIVEN BY AN ALTERNATING SIGNAL

This application is a continuation of International Patent Application No. PCT/EP2018/085734, filed Dec. 19, 2018, which claims priority to U.S. Provisional Application No. 62/610,932, filed Dec. 28, 2017, each of which is hereby incorporated by reference in its entirety for all purposes.

BACKGROUND

Nanopore membrane devices having pore sizes on the order of one nanometer in internal diameter have shown promise in rapid nucleotide sequencing. When a voltage signal is applied across a nanopore immersed in a conducting fluid, the electric field can move ions in the conducting fluid through the nanopore. The movement of ions in the conducting fluid through the nanopore can cause a small ion current. The voltage applied can also move the molecules to be sequenced into, through, or out of the nanopore. The level of the ion current (or a corresponding voltage) depends on the sizes and chemical structures of the nanopore and the particular molecule that has been moved into the nanopore.

As an alternative to a DNA molecule (or other nucleic acid molecule to be sequenced) moving through the nanopore, a molecule (e.g., a nucleotide being added to a DNA strand) can include a particular tag of a particular size and/or structure. The ion current or a voltage in a circuit including the nanopore (e.g., at an integrating capacitor) can be measured as a way of measuring the resistance of the nanopore corresponding to the molecule, thereby allowing the detection of the particular molecule in the nanopore, and the particular nucleotide at a particular position of a nucleic acid.

A nanopore based sequencing chip may be used for DNA sequencing. A nanopore based sequencing chip can incorporate a large number of sensor cells configured as an array. For example, an array of one million cells may include 1000 rows by 1000 columns of cells.

The voltages that are measured can vary from chip to chip and from cell to cell of a same chip due to manufacturing variability. Therefore, it can be difficult to determine the correct molecule, which may be or correspond to the correct nucleotide in a particular nucleic acid or other polymer in a cell.

Accordingly, improved techniques are desired for sequencing.

BRIEF SUMMARY

Various embodiments provide techniques and systems related to the processing of output signals from cells of a multi-cell nanopore-based sequencing chip. An improved multi-cell nanopore-based sequencing chip may be built by employing various embodiments disclosed herein. For example, embodiments can include systems and methods for performing sequencing signal processing that can compensate for non-idealities in the sequencing signal. The non-idealities can be caused by the occurrence of one or more states of the tag-nanopore system other than the threaded or open channel states. For example, noise that is caused by one or more intermediate states of the tag-nanopore system can be compensated for.

According to some embodiments, noise in the sequencing signal can be removed by using an improved signal processing technique that can discriminate between noise signal caused by, e.g., intermediate states and pure signal caused by, e.g., open channel and/or threaded states. The improved signal processing technique employs a period-to-period differencing scheme followed by a thresholding procedure to identify noise points and remove them from the sequencing signal. In one embodiment, the period-to-period difference signal is determined by time shifting an acquired sequencing signal by one AC period of the AC drive signal, and then subtracting the time shifted sequencing signal from the acquired signal. The difference signal will include portions having a high amplitude and/or variance and portions having a low amplitude and/or variance. A threshold can then be applied to the period-to-period difference signal as follows. Every point that is larger than the threshold is determined to be noise and then, the acquired sequencing signal data points that correspond to the noise points identified via the threshold in the period-to-period difference signal are removed from the acquired sequencing signal.

In some embodiments, more than one threshold can be used such that only those points that fall within the range of thresholds are identified as noise points and removed.

In some embodiments, the difference data can be filtered, smoothed, or otherwise denoised before comparison with the one or more thresholds to identify the noise points. For example, a wavelet based denoising technique can be applied to the period-to-period signal to generate a denoised period-to-period signal. The one or more thresholds are then applied to this denoised period-to-period signal to identify the set of noise peaks. In some embodiments, the wavelet based denoising technique can rely on Haar wavelets.

Other embodiments are directed to systems, portable consumer devices, and computer readable media associated with methods described herein.

A better understanding of the nature and advantages of embodiments of the present invention may be gained with reference to the following detailed description and the accompanying drawings.

TERMS

Figure 1:
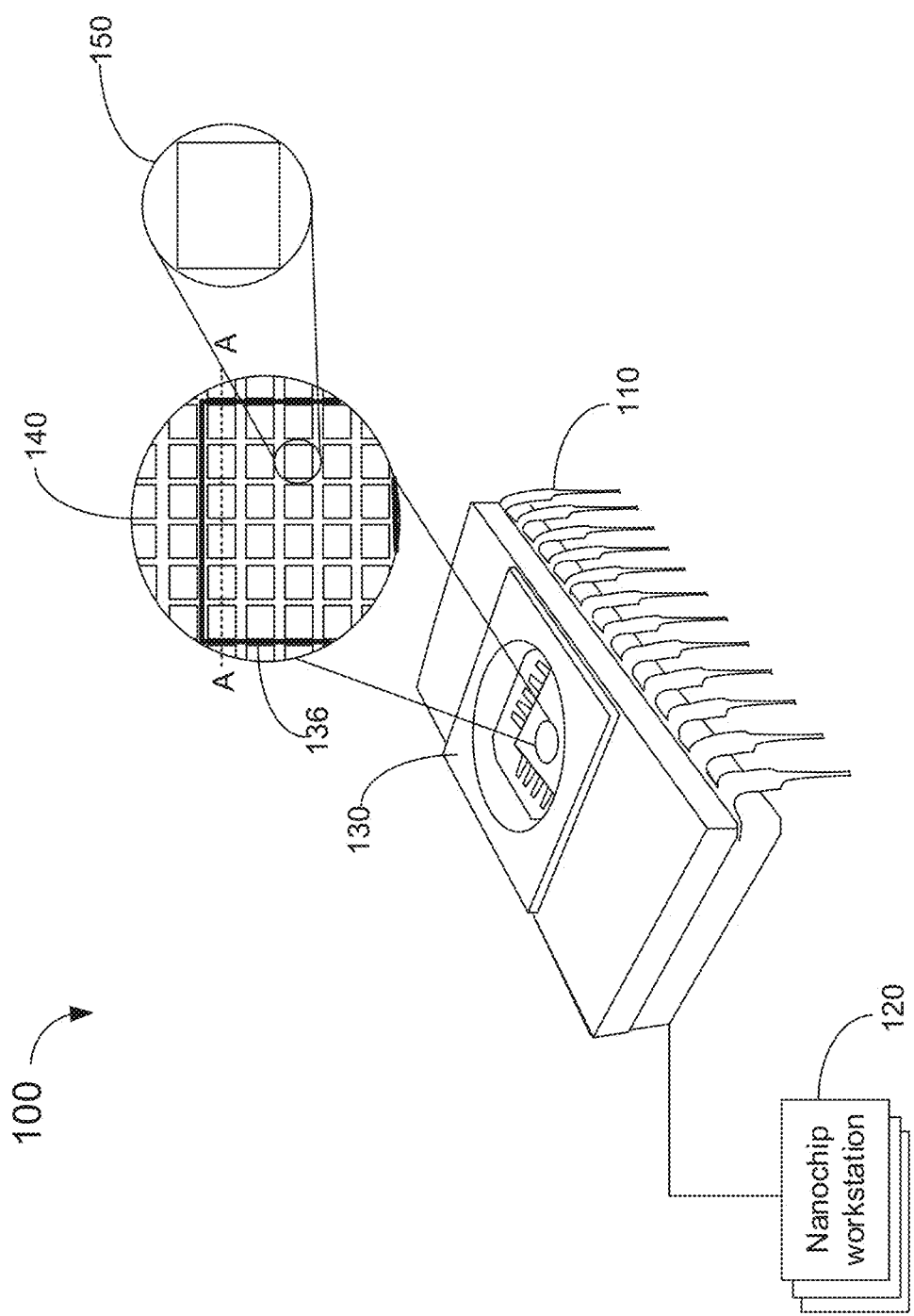
FIG. 1 is a top view of an embodiment of a nanopore sensor chip having an array of nanopore cells.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid may be used interchangeably with gene, cDNA, mRNA, oligonucleotide, and polynucleotide.

The term "template" may refer to a single stranded nucleic acid molecule that is copied into a complementary strand of DNA nucleotides for DNA synthesis. In some cases, a template may refer to the sequence of DNA that is copied during the synthesis of mRNA.

The term "primer" may refer to a short nucleic acid sequence that provides a starting point for DNA synthesis. Enzymes that catalyze the DNA synthesis, such as DNA polymerases, can add new nucleotides to a primer for DNA replication.

"Polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases $\alpha$, $\delta$, and $\epsilon$, are implicated in nuclear replication, and a family A polymerase, polymerase $\gamma$, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

"Nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. Some nanopores are proteins.

"Nucleotide," in addition to referring to the naturally occurring ribonucleotide or deoxyribonucleotide monomers, can be understood to refer to related structural variants thereof, including derivatives and analogs, that are functionally equivalent with respect to the particular context in which the nucleotide is being used (e.g., hybridization to a complementary base), unless the context clearly indicates otherwise.

"Tag" refers to a detectable moiety that can be atoms or molecules, or a collection of atoms or molecules. A tag can provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag can be attached to the nucleotide via the phosphate moiety.

As used herein, the term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different.

DETAILED DESCRIPTION

In a basic model, a nanopore-tag system of a sequencing cell can be in one of five states: the open channel state or one of the four threaded states for the tags corresponding to C, G, A, and T nucleotides. However, in practice, the dynamics of the nanopore-tag system can be more complex than this basic model and in addition to the four threaded states, several other intermediate states can lead to additional noise being added to the sequencing signal.

In general one or more embodiments can be used to remove noise from the sequencing signal, include noise caused by one or more intermediate states. For example, the signal processing techniques disclosed herein can take advantage of one or more differences between true signal (where the term "true signal" herein refers to sequencing signal caused by the open channel and threaded states) and noise signal caused by states other than the open or threaded channels, such as the intermediate states mentioned above. More specifically, embodiments can employ a period-to-period differencing technique that can be used to differentiate noise signal from true signal based on the observation that noise signal possess a significantly higher amplitude/variance in the period-to-period difference signal than the true signal. In other words, both the open channel and the threaded channel portions of the period-to-period difference signal possess a lower amplitude than the intermediate state portions of the period-to-period signal.

Accordingly, techniques disclosed herein provide for a method to separate the true signal from the noise by applying a threshold to the period-to-period difference signal and then identifying as noise the set of the period-to-period difference values that are greater than or equal to the threshdold value. Once the set of noise points in the period-to-period difference signal is identified, the original sequencing signal can be denoised by removing the points that are associated with the period-to-period noise points. This denoised sequencing signal can then be further processed, if necessary, and ultimately can be used as input to a base calling process that produces a more accurate nanopore based DNA sequence. As used herein the term denoised signal is intended to include a signal that includes less noise than the original. As such a denoised signal can still include residual noise without departing from the scope of the present disclosure.

I. Nanopore Based Sequencing Chip

FIG. 1 is a top view of an embodiment of a nanopore sensor chip 100 having an array 140 of nanopore cells 150. Each nanopore cell 150 includes a control circuit integrated on a silicon substrate of nanopore sensor chip 100. In some embodiments, side walls 136 may be included in array 140 to separate groups of nanopore cells 150 so that each group may receive a different sample for characterization. Each nanopore cell may be used to sequence a nucleic acid. In some embodiments, nanopore sensor chip 100 may include a cover plate 130. In some embodiments, nanopore sensor chip 100 may also include a plurality of pins 110 for interfacing with other circuits, such as a computer processor.

In some embodiments, nanopore sensor chip 100 may include multiple chips in a same package, such as, for example, a Multi-Chip Module (MCM) or System-in-Package (SiP). The chips may include, for example, a memory, a processor, a field-programmable gate array (FPGA), an application-specific integrated circuit (ASIC), data converters, a high-speed I/O interface, etc.

In some embodiments, nanopore sensor chip 100 may be coupled to (e.g., docked to) a nanochip workstation 120, which may include various components for carrying out (e.g., automatically carrying out) various embodiments of the processes disclosed herein, including, for example, analyte delivery mechanisms, such as pipettes for delivering lipid suspension or other membrane structure suspension, analyte solution, and/or other liquids, suspension or solids, robotic arms, computer processor, and/or memory. A plurality of polynucleotides may be detected on array 140 of nanopore cells 150. In some embodiments, each nanopore cell 150 can be individually addressable.

II. Nanopore Sequencing Cell

Nanopore cells 150 in nanopore sensor chip 100 may be implemented in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

A. Nanopore Sequencing Cell Structure

Figure 2:
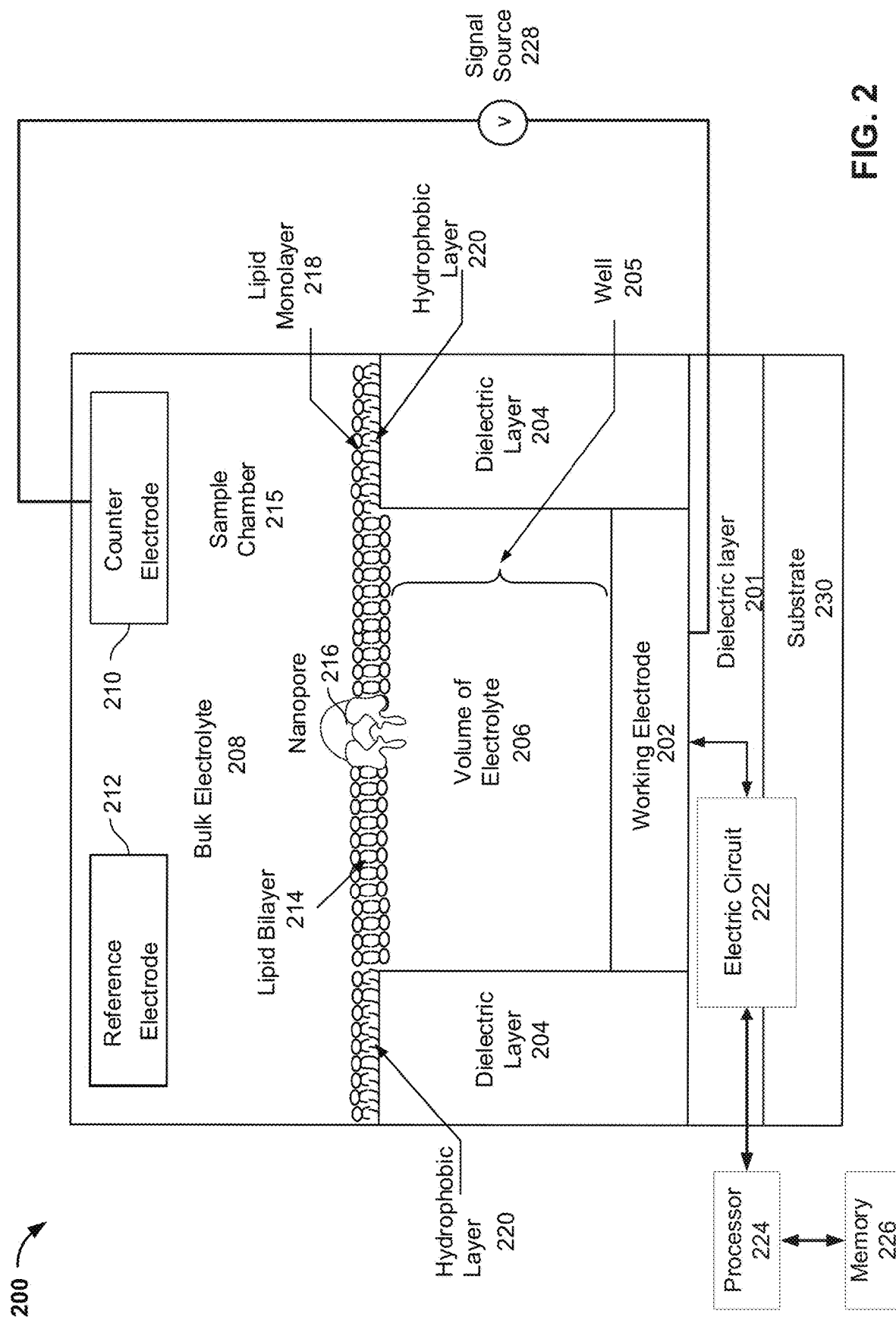
FIG. 2 illustrates an embodiment of a nanopore cell in a nanopore sensor chip that can be used to characterize a polynucleotide or a polypeptide.

FIG. 2 illustrates an embodiment of an example nanopore cell 200 in a nanopore sensor chip, such as nanopore cell 150 in nanopore sensor chip 100 of FIG. 1, that can be used to characterize a polynucleotide or a polypeptide. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the data detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array and may also provide one or more commands to electric circuit 222.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. Dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometer (nm).

Well 205 formed by the walls of dielectric layer 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns (μm).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer 218 may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy (polyethylene glycol)-1000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Counter electrode (CE) 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks can be made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, may enable parallel sequencing using a single molecule nanopore-based sequencing by synthesis (Nano-SBS) technique.

Figure 3:
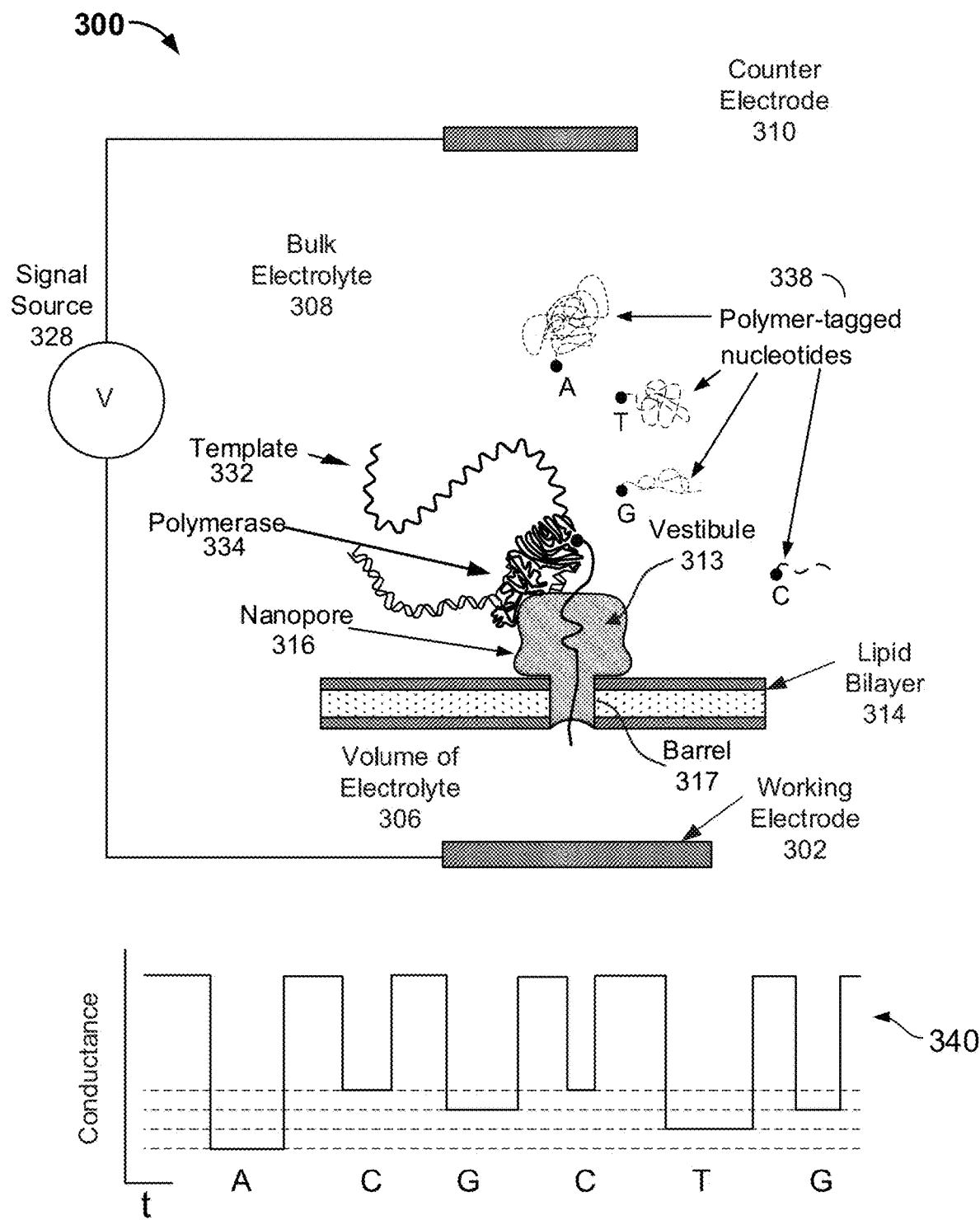
FIG. 3 illustrates an embodiment of a nanopore cell performing nucleotide sequencing using a nanopore-based sequencing-by-synthesis (Nano-SBS) technique.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C. When a tagged nucleotide is correctly complexed with polymerase 334, the tag may be pulled (loaded) into the nanopore by an electrical force, such as a force generated in the presence of an electric field generated by a voltage applied across lipid bilayer 314 and/or nanopore 316. The tail of the tag first enters the nanopore 316 via the vestibule 313 and then may be pulled into the barrel 317 of nanopore 316. The tag can then be held in the barrel 317 of nanopore 316 and generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10000 ms. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
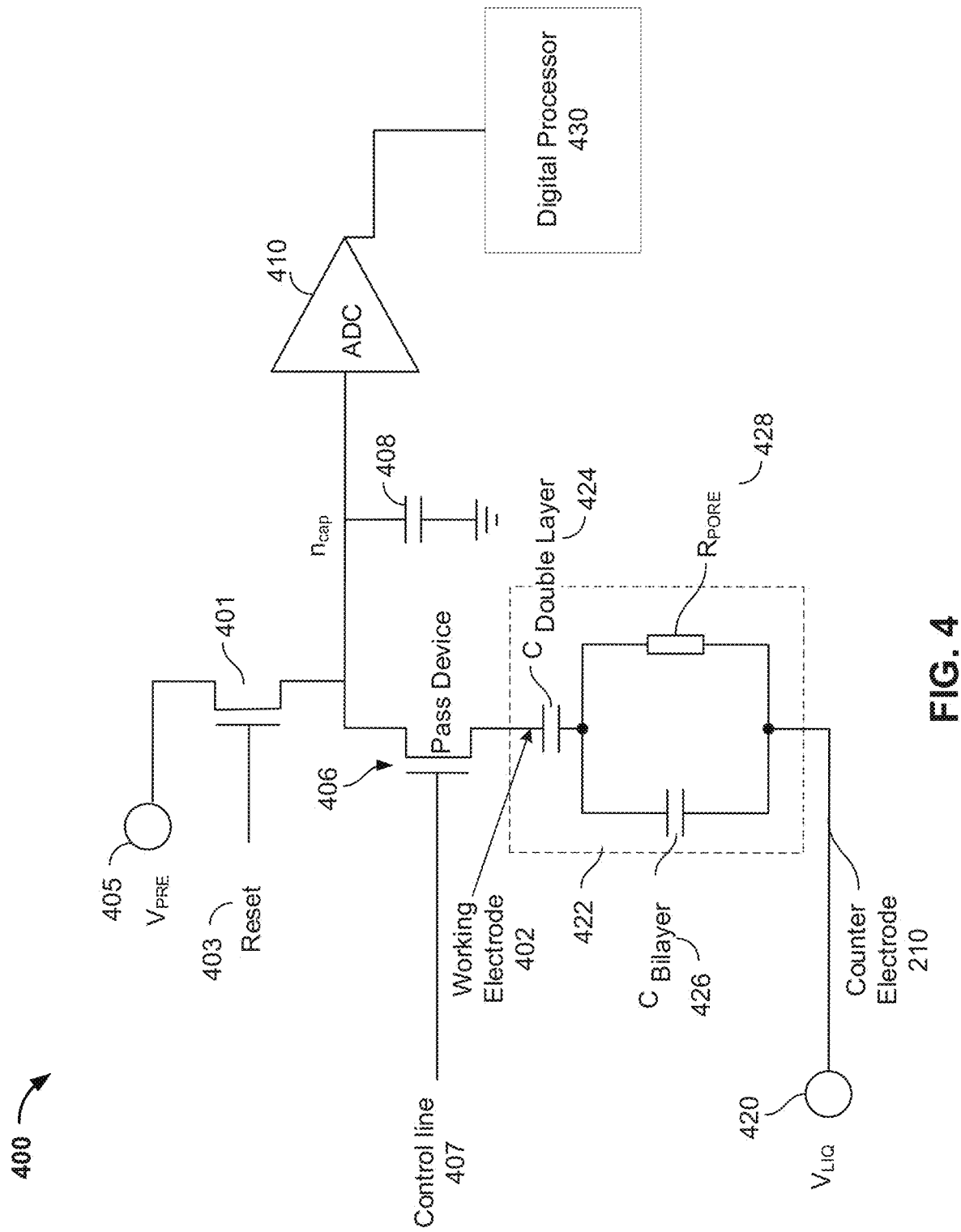
FIG. 4 illustrates an embodiment of an electric circuit in a nanopore cell.

FIG. 4 illustrates an embodiment of an electric circuit 400 (which may include portions of electric circuit 222 in FIG. 2) in a nanopore cell, such as nanopore cell 200. As described above, in some embodiments, electric circuit 400 includes a counter electrode 210 that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to an alternating voltage source 420 ($V_{LIQ}$). In some embodiments, an AC non-Faradaic mode may be utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 210 and the lipid bilayer (e.g., lipid bilayer 214) may be modeled by a large capacitor (not shown), such as, for example, 100 µF or larger.

FIG. 4 also shows an electrical model 422 representing the electrical properties of a working electrode (e.g., working electrode 202) and the lipid bilayer (e.g., lipid bilayer 214). Electrical model 422 includes a capacitor 426 ($C_{Bilayer}$) that models a capacitance associated with the lipid bilayer and a resistor 428 ($R_{PORE}$) that models a variable resistance associated with the nanopore, which can change based on the presence of a particular tag in the nanopore. Electrical model 422 also includes a capacitor 424 having a double layer capacitance ($C_{Double\ Layer}$) and representing the electrical properties of working electrode 202 and well 205. Working electrode 202 may be configured to apply a distinct potential independent from the working electrodes in other nanopore cells.

Pass device 406 is a switch that can be used to connect or disconnect the lipid bilayer and the working electrode from electric circuit 400. Pass device 406 may be controlled by control line 407 to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 may be kept open to avoid a short-circuit condition. Pass device 406 may be closed after lipid solvent has been deposited to the nanopore cell to seal the well of the nanopore cell.

Electric circuit 400 may further include an on-chip integrating capacitor 408 ($n_{cap}$). Integrating capacitor 408 may be pre-charged by using a reset signal 403 to close switch 401, such that integrating capacitor 408 is connected to a voltage source $V_{PRE}$ 405. In some embodiments, voltage source $V_{PRE}$ 405 provides a constant reference voltage with a magnitude of, for example, 900 mV. When switch 401 is closed, integrating capacitor 408 may be pre-charged to the reference voltage level of voltage source $V_{PRE}$ 405.

After integrating capacitor 408 is pre-charged, reset signal 403 may be used to open switch 401 such that integrating capacitor 408 is disconnected from voltage source $V_{PRE}$ 405. At this point, depending on the level of voltage source $V_{LIQ}$, the potential of counter electrode 210 may be at a level higher than the potential of working electrode 202 (and integrating capacitor 408), or vice versa. For example, during a positive phase of a square wave from voltage source $V_{LIQ}$ (e.g., the bright or dark period of the AC voltage source signal cycle), the potential of counter electrode 210 is at a level higher than the potential of working electrode 202. During a negative phase of the square wave from voltage source $V_{LIQ}$ (e.g., the dark or bright period of the AC voltage source signal cycle), the potential of counter electrode 210 is at a level lower than the potential of working electrode 202. Thus, in some embodiments, integrating capacitor 408 may be further charged during the bright period from the pre-charged voltage level of voltage source $V_{PRE}$ 405 to a higher level, and discharged during the dark period to a lower level, due to the potential difference between counter electrode 210 and working electrode 202. In other embodiments, the charging and discharging may occur in dark periods and bright periods, respectively.

Integrating capacitor 408 may be charged or discharged for a fixed period of time, depending on the sampling rate of an analog-to-digital converter (ADC) 410, which may be higher than 1 kHz, 5 kHz, 10 kHz, 100 kHz, or more. For example, with a sampling rate of 1 kHz, integrating capacitor 408 may be charged/discharged for a period of about 1 ms, and then the voltage level may be sampled and converted by ADC 410 at the end of the integration period. A particular voltage level would correspond to a particular tag species in the nanopore, and thus correspond to the nucleotide at a current position on the template.

After being sampled by ADC 410, integrating capacitor 408 may be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 410 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 can perform further downstream processing, such as base determination. Digital processor 430 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore, also referred to herein as the unthreaded state of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore may result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant $\tau=RC$, where R is the resistance associated with the nanopore (i.e., $R_{PORE}$ 428) and C is the capacitance associated with the membrane (i.e., capacitor 426 ($C_{Bilayer}$)) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MOhm to 20 GOhm. In some embodiments, the resistance associated with the nanopore in a state where a tag is inside the barrel of the nanopore may be within the range of 200 MOhm to 40 GOhm. In other embodiments, integrating capacitor 408 may be omitted, as the voltage leading to ADC 410 will still vary due to the voltage decay in electrical model 422.

The rate of the decay of the voltage on integrating capacitor 408 may be determined in different ways. As explained above, the rate of the voltage decay may be determined by measuring a voltage decay during a fixed time interval. For example, the voltage on integrating capacitor 408 may be first measured by ADC 410 at time t1, and then the voltage is measured again by ADC 410 at time t2. The voltage difference is greater when the slope of the voltage on integrating capacitor 408 versus time curve is steeper, and the voltage difference is smaller when the slope of the voltage curve is less steep. Thus, the voltage difference may be used as a metric for determining the rate of the decay of the voltage on integrating capacitor 408, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including current measurement techniques.

In some embodiments, electric circuit 400 may not include a pass device (e.g., pass device 406) and an extra capacitor (e.g., integrating capacitor 408 ($n_{cap}$)) that are fabricated on-chip, thereby facilitating the reduction in size of the nanopore-based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 may be used as the integrating capacitor, and may be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integrating capacitor (e.g., integrating capacitor 408 ($n_{cap}$) or capacitor 426 ($C_{Bilayer}$)) can be sampled and converted by the ADC (e.g., ADC 410) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integrating capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{LIQ}$ is lower than $V_{PRE}$, which may correspond to a bright mode (period) where the tag is forced into the barrel of the nanopore. Another subset may correspond to a dark mode (period) where the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($C_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values may deviate from $V_{LIQ}$ as the working electrode charges. The rate of change of the voltage level on the integrating capacitor may be governed by the value of the resistance of the bilayer, which may include the nanopore, which may in turn include a molecule (e.g., a tag of a tagged nucleotides) in the nanopore. The voltage level can be measured at a predetermined time after switch 401 opens.

Switch 401 may operate at the rate of data acquisition. Switch 401 may be closed for a relatively short time period between two acquisitions of data, typically right after a measurement by the ADC. The switch allows multiple data points to be collected during each sub-period (bright or dark) of each AC cycle of $V_{LIQ}$. If switch 401 remains open, the voltage level on the integrating capacitor, and thus the output value of the ADC, would fully decay and stay there. Instead, when switch 401 is closed, the integrating capacitor is precharged again (to $V_{PRE}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

Figure 5:
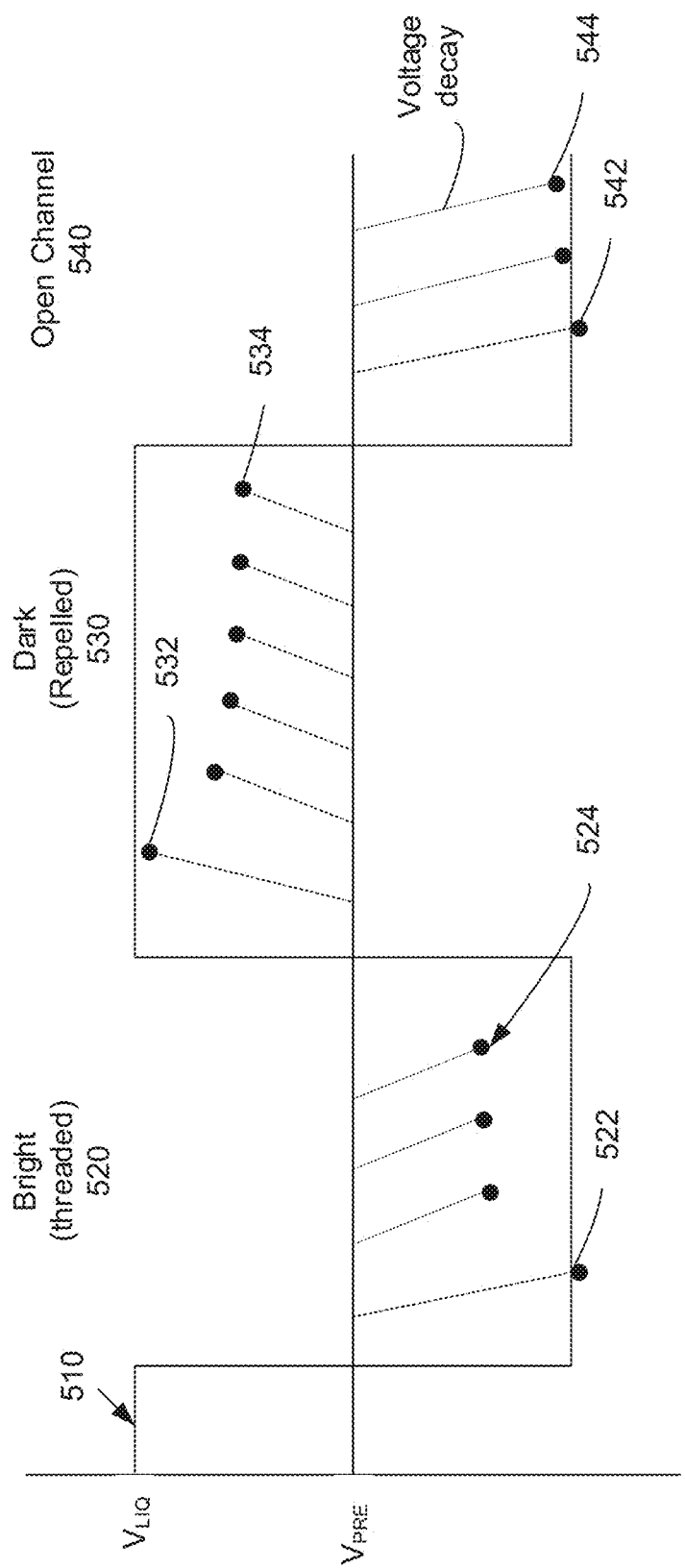
FIG. 5 shows example data points captured from a nanopore cell during bright periods and dark periods of AC cycles, according to certain aspects of the present disclosure.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle may be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 may be closed and the voltage at the measurement node will increase back to $V_{PRE}$ again. The process can repeat to measure multiple voltage data points. In this way, multiple data points may be captured during the bright period.

As shown in FIG. 5, a first data point 522 (also referred to as first point delta (FPD)) in the bright period after a change in the sign of the $V_{LIQ}$ signal may be lower than subsequent data points 524. This may be because there is no tag in the nanopore (open channel), and thus it has a low resistance and a high discharge rate. In some instances, first data point 522 may exceed the $V_{LIQ}$ level as shown in FIG. 5. This may be caused by the capacitance of the bilayer coupling the signal to the on-chip capacitor. Data points 524 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 may decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 may be closed and the voltage at the measurement node will decrease back to $V_{PRE}$ again. The process can repeat to measure multiple voltage data points. Thus, multiple data points may be captured during the dark period, including a first point delta 532 and subsequent data points 534. As described above, during the dark period, any nucleotide tag is pushed out of the nanopore, and thus minimal information about any nucleotide tag is obtained, besides for use in normalization.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

4. Determining Bases

For each usable nanopore cell of the nanopore sensor chip, a production mode can be run to sequence nucleic acids. The ADC output data captured during the sequencing can be normalized to provide greater accuracy. Normalization can account for offset effects, such as cycle shape and baseline shift. After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

Further details regarding the sequencing operation can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," the disclosures of which are incorporated by reference in their entirety for all purposes.

5. Periodicity of Voltage Values

Figure 6:
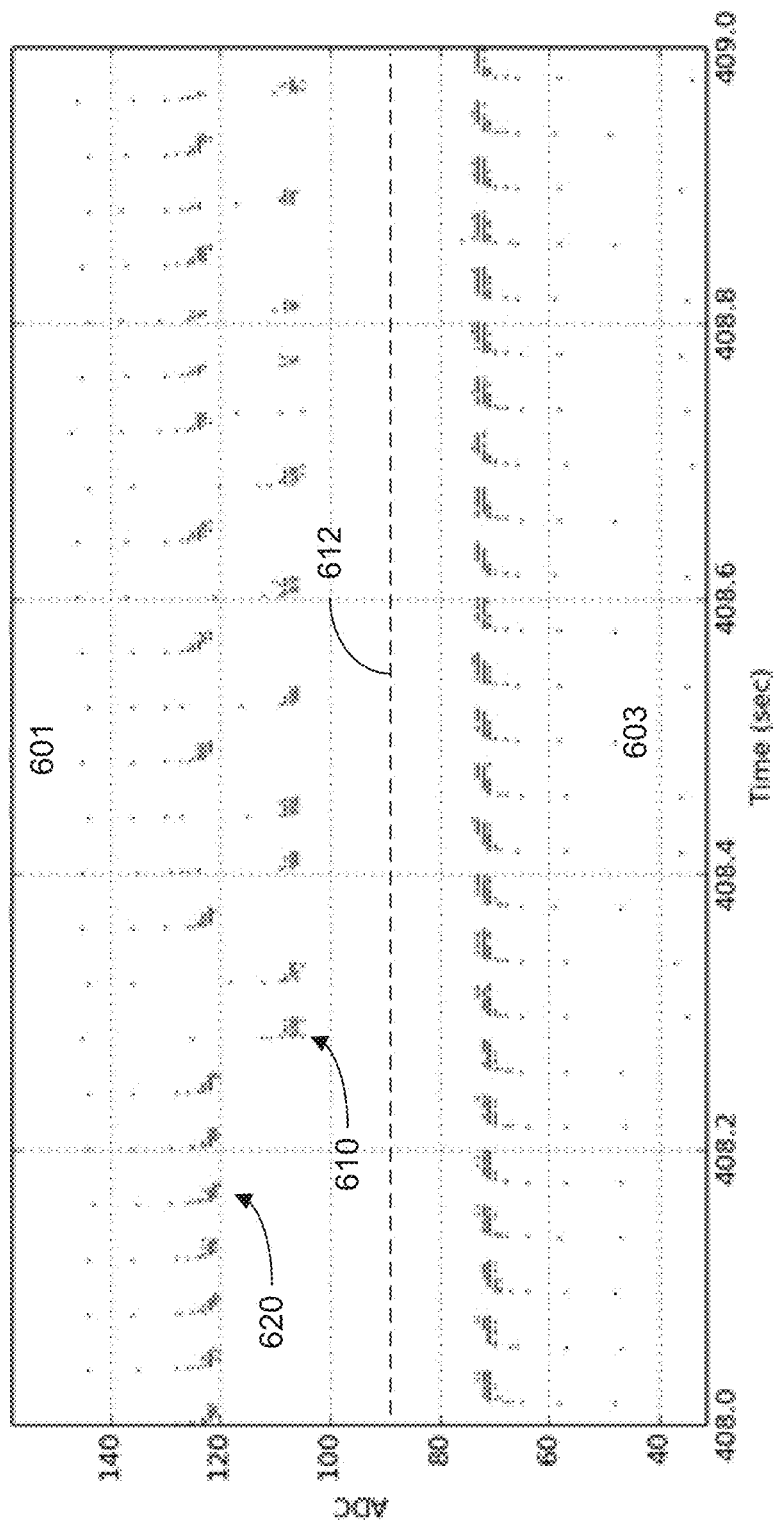
FIG. 6 shows sample data that illustrates the periodicity of voltage data, according to certain aspects of the present disclosure.

FIG. 6 shows sample bright and dark period data for a test sequencing run according to some embodiments. Bright period data are shown on top portion 601 of the figure and the dark period data are shown on the bottom portion 603 of the figure. The periodicity of the voltage data is caused by an alternating signal provided by an alternating (AC) voltage source, e.g., AC voltage source 420, as described above in reference to FIG. 4. Each data point shown in FIG. 6 is obtained by an ADC measurement of the voltage on a node of the nanopore cell circuit, e.g., at $n_{cap}$ in FIG. 4, after a certain period of time relative to the opening of pass device 406. For each measurement, the voltage at $n_{cap}$ starts at $V_{PRE}$ ($V_{PRE}$ is shown as dashed line 612) and then decays, approaching +/−$V_{LIQ}$ depending on the period (bright or dark) within the AC cycle. After a certain time delay, the ADC measures a voltage value. FIG. 6 shows the collection of these measured voltage values, i.e., each data point is a single point sample of the RC decay curve from $V_{PRE}$ to $V_{LIQ}$. For the example shown in FIG. 6, the data acquisition rate is about 1,976 Hz. Within each period, the variation in voltage from point-to-point is caused, in part, by charge buildup in the cell, leading to an overall shift in the underlying voltage decay curve for the charging/discharging of the integrating capacitor (e.g., capacitor 408 or capacitor 426, depending on the circuit used).

FIG. 6 shows data from an open channel state of the bright mode, e.g., bright mode data 620 that precedes a threading event 610 that appears shortly after the start of the bright period of the $7^{th}$ AC cycle. Subsequent open channel values and threading events in other AC cycles are also shown as time progresses. In some embodiments, as shown here, the measured ADC values in the bright periods are actually fairly repeatable from cycle to cycle for both threaded and open channel states. This opens up the possibility that the systematic offsets and noise in one bright period's data may be compensated using an adjacent (or even a subsequent non-adjacent) bright period's data, without the need to use dark channel data. The following section details one or more embodiments that make use of the periodicity of the voltage data.

III. Identifying and Characterizing Noise Using Period-to-Period Difference Signal In an idealized scenario, the nanopore-DNA-tag system of a sequencing cell can be in one of five states: the open channel state or one of the four the threaded states for the tags corresponding to C, G, A, and T. As discussed above in reference to FIG. 3, during a threading event, the tail of a tag can first enter the nanopore 316 via the vestibule 313 and then the tail may be pulled into the barrel 317 of nanopore 316. As the tag is held within the barrel 317 of nanopore 316, a unique ionic blockade signal is generated thereby electronically identifying the added base to which the tag is attached.

However, in practice, the dynamics of the nanopore-DNA-tag system can be more complex than the ideal threading dynamics described above and these non-idealities can lead to additional noise being added to the ionic blockade signal. For example, a tag can very quickly pass through the nanopore without being held in the barrel. F, or may enter the barrel only briefly before exiting again via the vestibule. In addition, a tag can enter into the vestibule and persist there in a folded configuration that does not allow the tag to be effectively pulled into the barrel. In this case, the folded tag may be held in the vestibule for a period of time before exiting the nanopore via the vestibule again. Many possible intermediate states of the nanopore-DNA-tag are possible and each may contribute to noise on the sequencing signal. In some cases, these so-called "intermediate states" can even possess signal values that are equal to or nearly equal to the expected threaded channel values, and can therefore be inadvertently identified as a threaded base leading to downstream sequencing errors. Other possible intermediate states of a related system are described in Maglia et al., *Enhanced Translocation of Single DNA Molecules Through α-Hemolysin Nanopores by Manipulation of Internal Charge*, Proc Natl Acad Sci U.S.A. 2008 Dec. 16; 105(50): 19720-19725. While these state are referred to herein as intermediate states it should be understood that any non-threaded or non-open channel state can contribute to noise on the sequencing signal and, as such, embodiments of the present disclosure are not limited to noise sources having the particular physical sources described herein.

In some cases, the timescales for the physical dynamics the intermediate states can differ from the timescales associated with bona-fide threading events. In addition, and somewhat relatedly, the variance in amplitude of the sequencing signal over time during an intermediate state can differ from the variance over time during both an open channel states and/or the four threaded channel states. Advantageously, signal processing techniques disclosed herein can take advantage of the differences, e.g., in timescale and variance, between true signal (open channel and/or threaded signal) and noise signal (caused by other states, including intermediate states described above) and these techniques can be used to de-noise the sequencing signal. More specifically, according to certain embodiments, a period-to-period differencing technique can be used to identify portions of the sequencing signal that include noise so that these points can be removed leaving a de-noised signal that includes a higher fraction of point that are either open channel or threaded states.

A. Introduction to the Period-to-Period Differencing Method

According to certain embodiments, noise signal can be identified and analyzed using a technique referred to herein as period-to-period differencing. One form of period-to-period differencing is described within co-pending U.S. patent application Ser. No. 15/628,353, the disclosure of which is incorporated by reference in its entirely for all purposes. According to certain embodiments, to determine a period-to-period difference signal, also referred to herein as "difference data" one cycle of data can be subtracted from another cycle of data. For example, corresponding data points originating from a neighboring cycle can be subtracted from each other (e.g., nearest neighbor, second neighbor, etc.) to obtain the difference data as described in further detail below.

Figure 7:
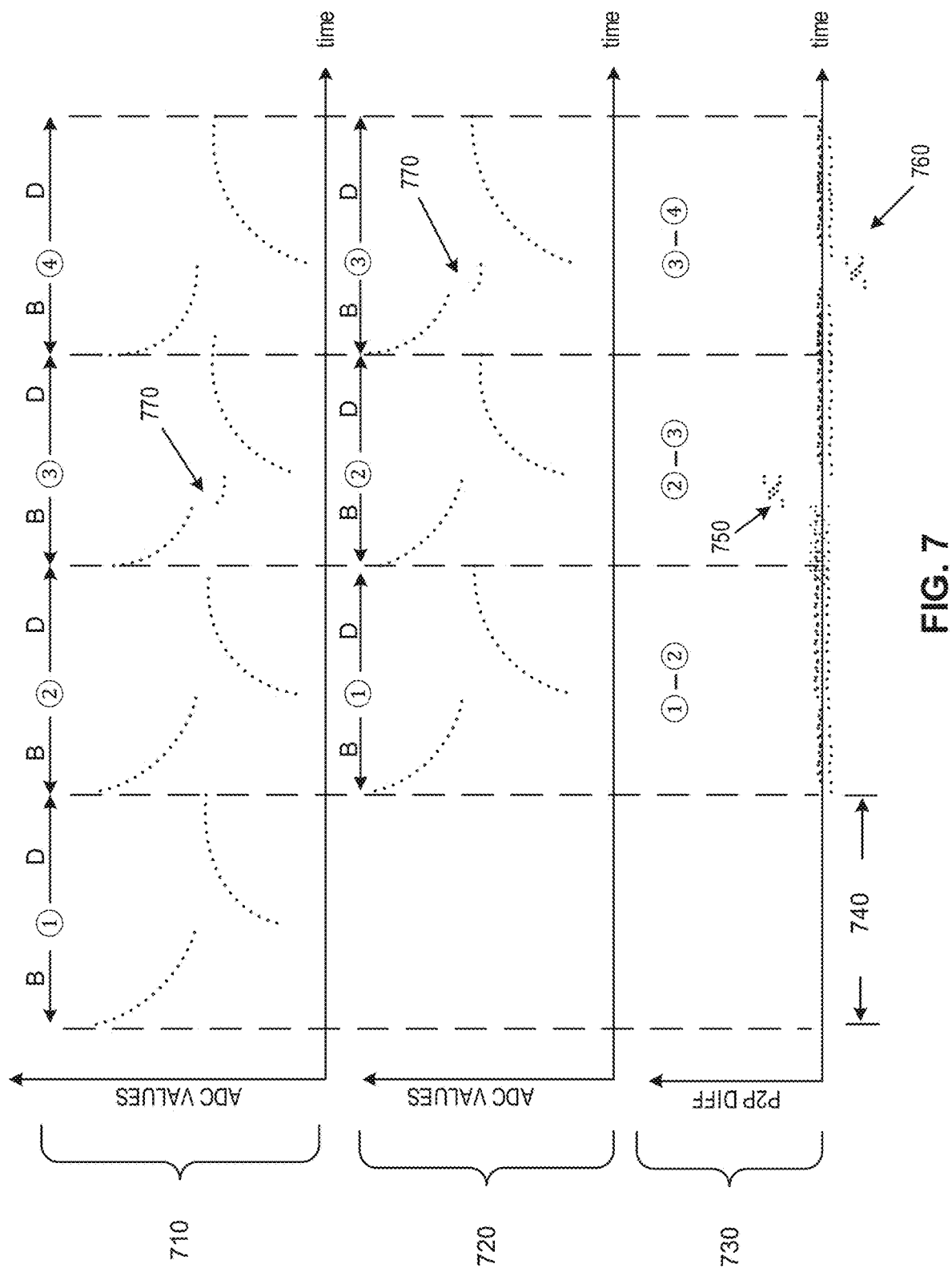
FIG. 7 illustrates shifting of voltage data for determining difference data, where the voltage data has one threading event, according to certain aspects of the present disclosure.

FIG. 7 shows sets of data points of multiple cycles 1-4, with each cycle having a respective bright and dark period, denoted by B and D labels located at the top of each plot in FIG. 7. Two shifted data sets can be generated from the raw sequencing data, and each may be stored in memory. Signal 710 is the raw data shifted by one-half period to the left (referred to herein as left_adc) and data 720 is the raw data shifted one-half period to the right (referred to herein as right_adc). While this embodiment shows an example of a net one-period shift, other shifts are possible without departing from the scope of the present disclosure, e.g., two-period shifts, three-period shifts, etc. Further, the raw data can be used, along with shifted data that is shifted one full period, as opposed to shifting twice at a half-period. The processed difference data 730 (referred to herein as p2p_diff) can then be created by subtracting the two shifted adc-signals, in this case:

$$p2p\_diff = left\_adc - right\_adc \qquad (1)$$

In some embodiments, the first cycle of processed difference data 730 (p2p_diff) is obtained by subtracting raw cycle 2 from raw cycle 1. The second cycle of processed difference data 730 (p2p_diff) is obtained by subtracting raw cycle 3 from raw cycle 2. The third cycle of processed difference data 730 (p2p_diff) is obtained by subtracting raw cycle 3 from raw cycle 4 and so on. In the processed difference data 730, the single threading event 770 from the raw data is duplicated, first appearing as a positive peak (event peak 750) and subsequently appearing again as a negative peak (event peak 760).

One of ordinary skill will appreciate that event peaks 750 and 760 are generally of opposite sign and thus, the positive and negative qualifiers are used herein as merely one example. The positive and negative peaks for this single threading event are separated in time by an amount that equals the net time shift between the two shifted data sets (one full period in this example). However, the net time shift may be longer for threading events that persist for multiple cycles.

While FIG. 7 shows a point-wise period-to-period differencing method to compute the processed difference data 730, any differencing scheme may be used without departing from the scope of the present disclosure, e.g., shifts may be in either direction (right-to-left or left-to-right) by a single or multiple of a period. FIG. 7 shows a nearest-neighbor difference by (net) shifting left-to-right by a single period. However, differences can be taken by shifting by a multiple of periods which can be provide more coarse scale information about the underlying signal.

A difference for the first cycle and/or last cycle may not be determined because there may be no first cycle data or last cycle data for one of the shifted cycles. Accordingly, these regions are referred to herein as "invalid regions." An example of a first invalid region 740 is shown in FIG. 7.

Figure 8:
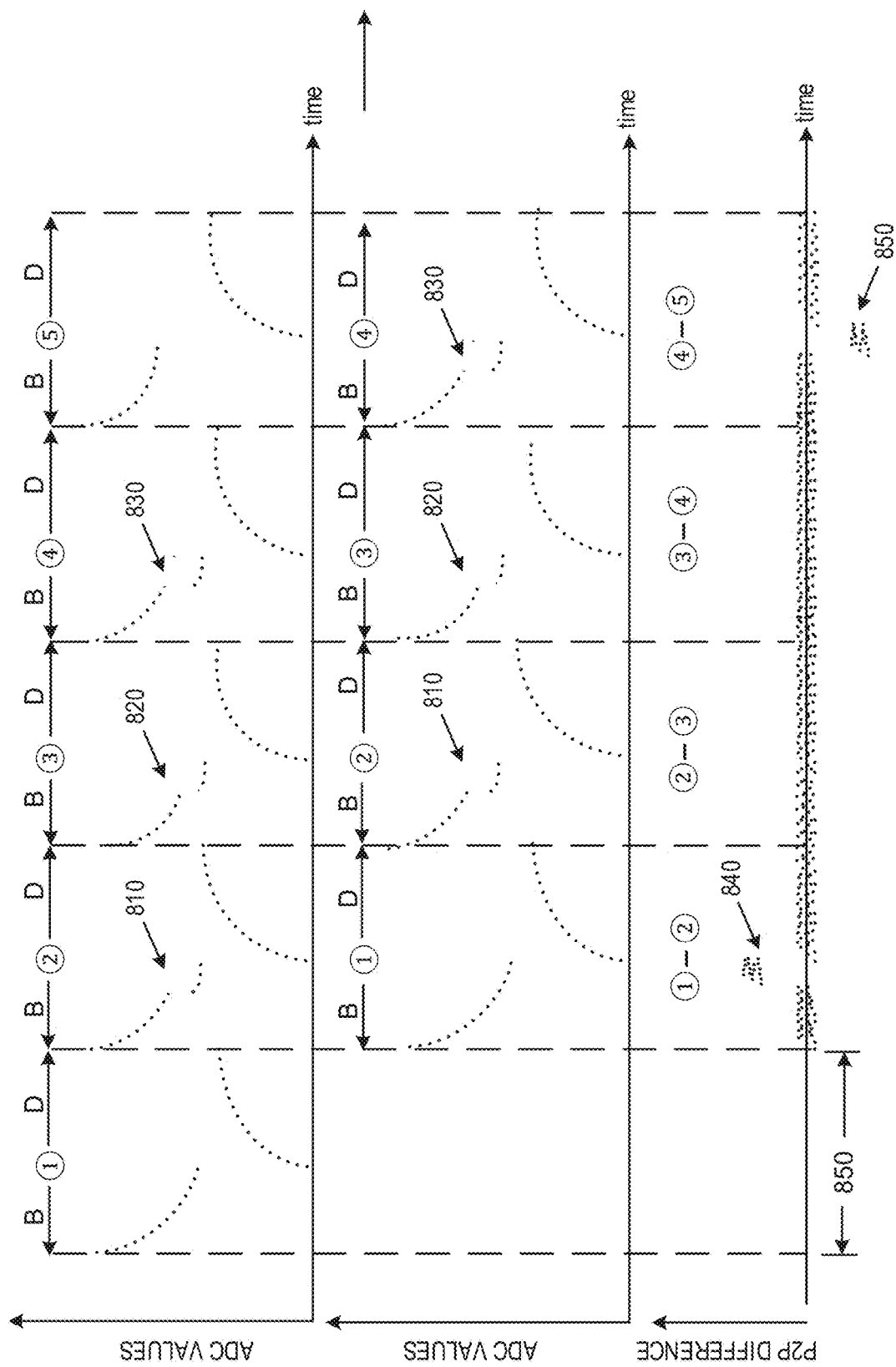
FIG. 8 illustrates shifting of voltage data for determining difference data, where the voltage data has three threading events, according to certain aspects of the present disclosure.

FIG. 8 illustrates an embodiment of the differencing technique, using the same shift method described in FIG. 7 above, but this time having raw data of a slightly different nature. As shown here, in some embodiments, a threading event may last more than one AC cycle. For example, in the data of FIG. 8, the threading event lasts three cycles, shown by threading events 810, 820, and 830 each occurring during cycles 2, 3, and 4, respectively. However, due to the repeatability in the raw data for each of these threading events, only the first threading event 810 and the last threading event 830 may appear in the processed difference data as positive peak 840 and negative peak 850, respectively.

B. Characterizing the Noise Signal Using Period-to-Period Differencing

To illustrate how to the period-to-period differencing technique described above can be used to differentiate noise signal from sequencing signal, consider a case of an open-channel pore under noiseless conditions. In such a condition, bright mode values from subsequent periods of the AC signal will be equal (assuming no gain drift and no offset drift). Stated more mathematically, consider the open channel signal acquired at a time t to be given by $OC_t(i)$ and the noiseless signal acquired during a subsequent period (t=t+nT), where T is the period of the AC signal and n is an integer) to be given by $OC_{t+nT}(i)$. Then, the period-to-period difference signal can be written as $$D_{p\text{-}to\text{-}p}(i)=OC_{t+nT}(i)-OC_t(i) \quad (2)$$

In the ideal case where the open channel level does not drift from period to period, $OC_{t+nT}(i)=OC_t(i)$ and therefore $$D_{p_{to}p}(i) = 0$$

for all i. In other words, in this ideal case, a period-to-period difference between bright mode signals from different periods of the AC signal should be zero for all time.

If random noise is now added to the bright mode signal, there is no guarantee that the noise added to one point in the first period is the same as noise added to a corresponding point in the second period. Stated mathematically, the noisy signal at time t is given by $OC_t(i)+\delta n_t(i)$ and the noisy signal at any subsequent cycle is given by $OC_{t+nT}(i)+\delta n_{t+nT}(i)$, where $\delta n_t(i)$ and $\delta n_{t+nT}(i)$ represent the noise on the signal at time t and at time t+nT, n periods later. In this case, the difference signal will no longer be zero, but rather will be given by the difference between the noise terms:

$$D_{p\text{-}to\text{-}p}(i)=\delta n_{t+nT}(i)-\delta n_t(i). \quad (3)$$

The precise value for the magnitude $D_{p\text{-}to\text{-}p}$ in the case of a noisy signal will in general depend on the timescale of the dynamics of the noise (in comparison to the period T of the AC signal), the amplitude of the noise, and the form of the probability distribution that describes the noise source.

The threaded case is similar to the open channel case described above because a threading event often will repeat for several cycles of the AC signal. Thus, in a noise free system, the difference signal would have one positive peak followed by several cycles of zeros and then a negative peak (or vice versa depending on the shift between the two signals). However, after adding in noise, there will be a non-zero period-to-period difference signal within the intervening region between the positive and negative peaks. Such a case was shown above in FIG. 8, where the threading event persists over three cycles of the AC signal (cycles 2-4) and the period-to-period difference signal shows a positive peak 840 marking the beginning of the threading event followed by a negative peak 850 marking the end of the threading event. The intervening points between the positive peak 840 and negative peak 850 are centered on zero but possess fluctuations about zero that correspond to the noise on the sequencing signal during the threading event.

In view of Eqn. (3) the amplitude of the period-to-period difference signal $D_{p\text{-}to\text{-}p}(i)$ can depend on the amplitude of the noise and as such can be used as a measure of the noise on the signal. Those parts of the signal that possess a high amplitude $D_{p\text{-}to\text{-}p}(i)$ are more likely to be noise while those portions of the signal with a low amplitude $D_{p\text{-}to\text{-}p}(i)$ are likely to be true signal (open channel or threading events). FIGS. 9-11 show samples of test data to further illustrate the above point.

Figure 9A:
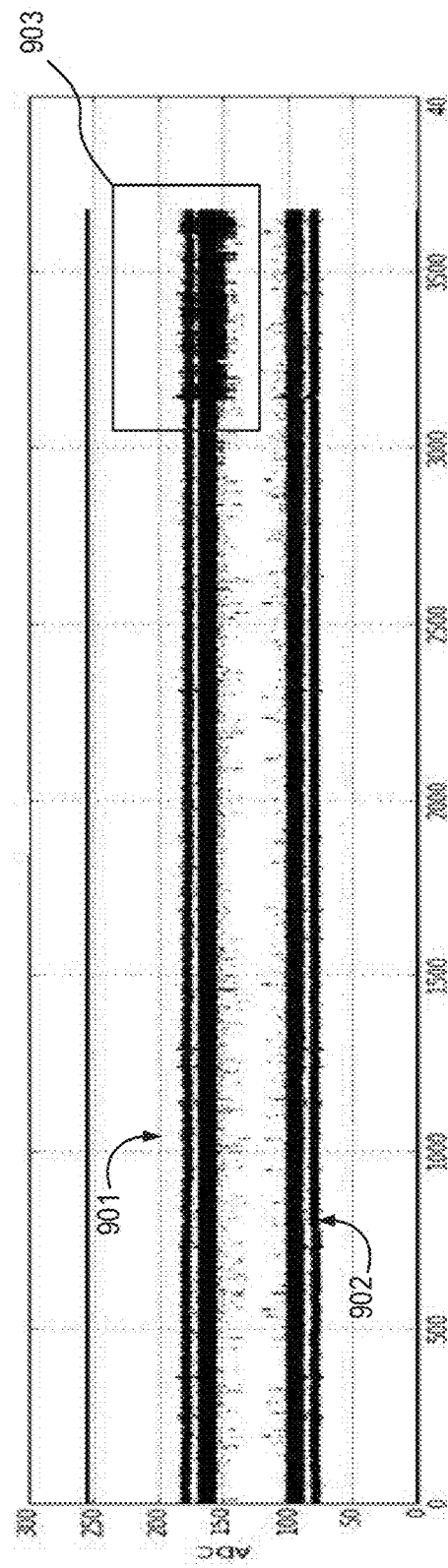
FIGS. 9A-9B illustrate sample raw sequencing signals under the influence of a noise source referred to herein as Pseudo-Threading Background Noise (PTBN), according to certain aspects of the present disclosure.
Figure 9B:
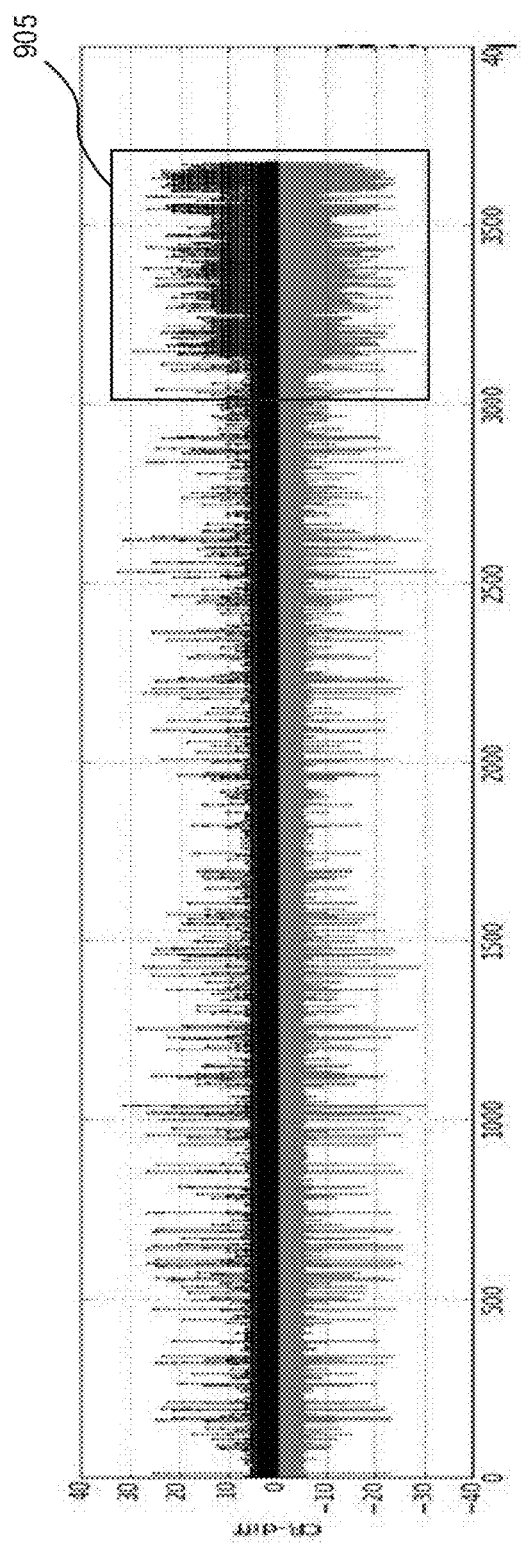

FIGS. 9A-9B show sample raw sequencing signal under the influence of a noise source referred to herein as Pseudo-Threading Background Noise (PTBN). The plot in FIG. 9A shows both bright mode data 901 and dark mode data 902 in a case where no threading events have occurred. Thus, the entirety of the bright mode data 901 includes only open channel signal values. However, in the last 500 ms of the bright mode data 901 PTBN begins to occur, as highlighted by the bright mode data shown within frame 903. Even though the system is still in the open channel state, PTBN results in signal values that are very close to or even equal to the levels that represent a valid threading event. Thus, if PTBN is not removed prior to base calling, sequencing errors can result.

FIG. 9B shows a period-to-period difference signal computed from the bright mode signal data 901. FIG. 9B clearly shows that the amplitudes of most of the points in the period-to-period difference signal are significantly higher during the time period when PTBN is occurring (during the time period from approximately 3.1 s to 3.3 s). On the other hand, during a normal open channel state (during the time period from approximately 0 s to 3.1 s), the amplitudes of most of the points in the period-to-period signal is lower. Accordingly, one or more points in the sequencing signal can be identified as high probability PTBN noise points by identifying the points in the period-to-period difference signal that have an amplitude above a threshold level. Once these points are identified, they can be removed from the original signal to produce a denoised signal, as described in further detail below in reference to FIGS. 11-13.

Figure 10A:
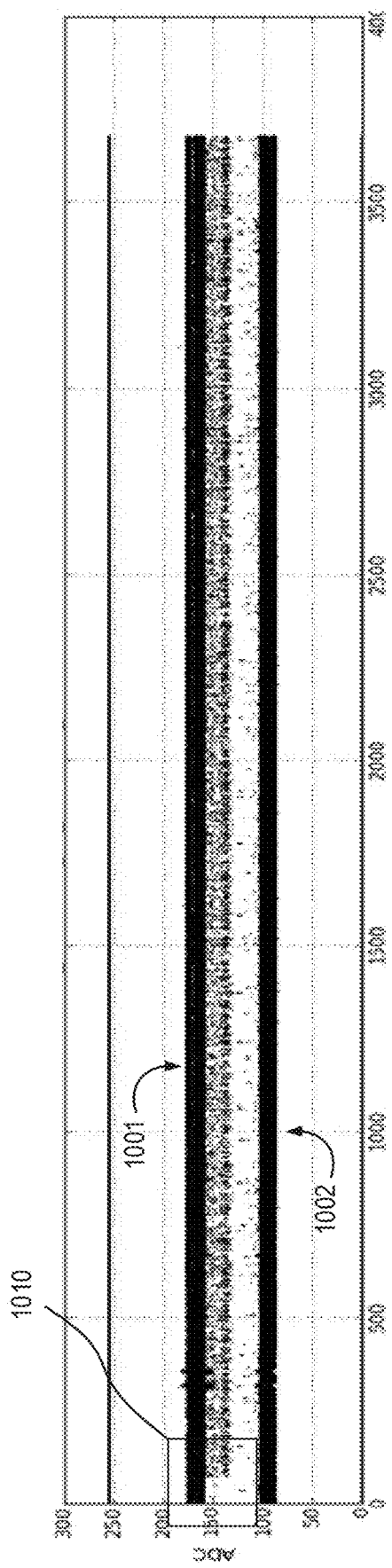
FIGS. 10A-10B illustrate sample raw sequencing signals, this time under the influence of a noise source known as Fast Capture Noise (FCN), according to certain aspects of the present disclosure.
Figure 10B:
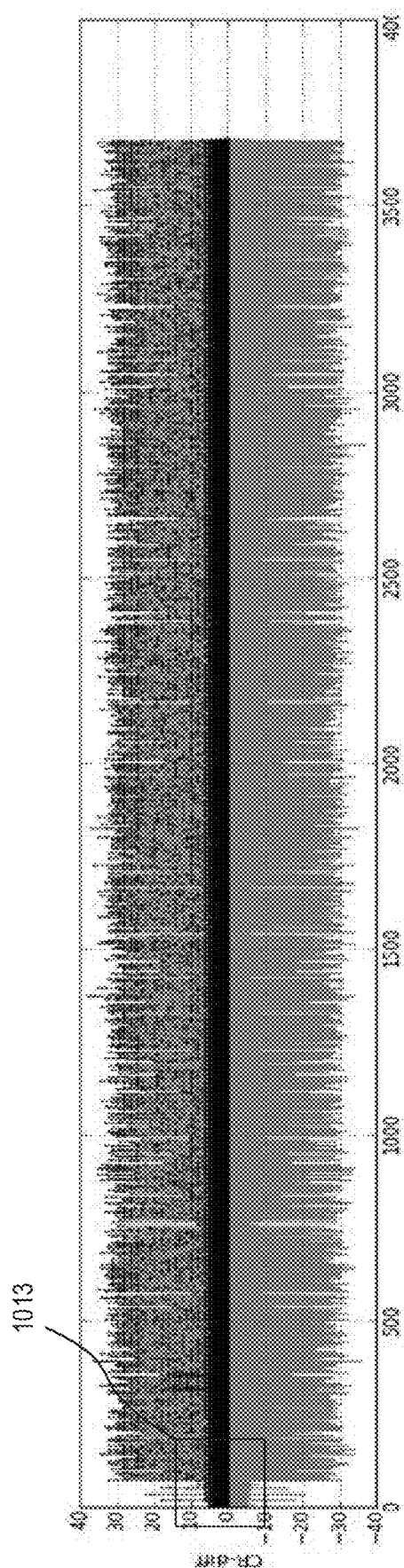
Figure 11:
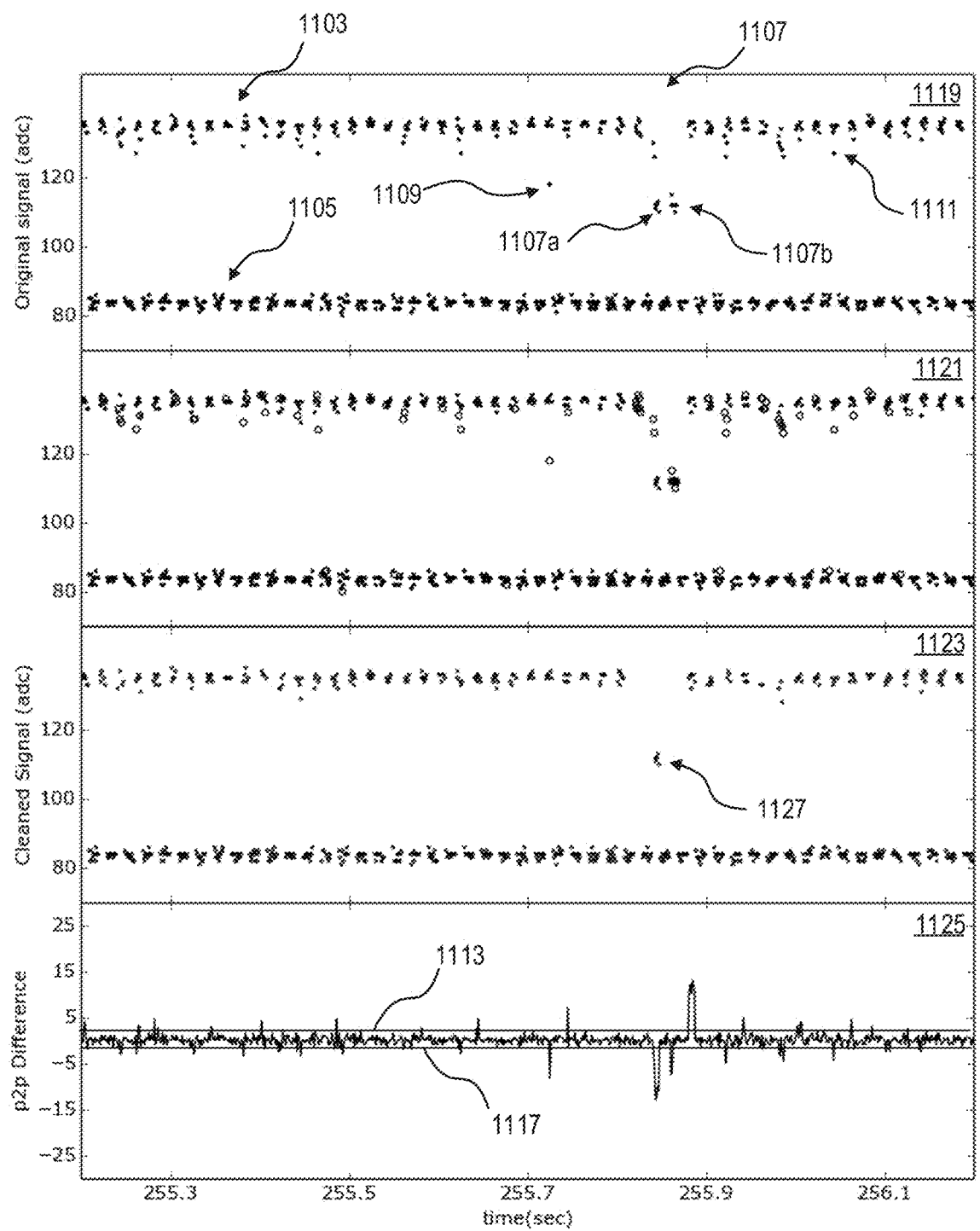
FIG. 11 illustrates how a raw sequencing signal can be de-noised using a thresholding technique, according to certain aspects of the present disclosure.

FIGS. 10A-10B show sample raw sequencing signal under the influence of a noise source referred to herein as Fast Capture Noise (FCN). In some cases, a type of FCN can be caused as a result of a fast kinetics collision of a tag with a pore. For example, FCN can occur if a tag repetitively enters the vestibule of a nanopore but then, before the tag is fully threaded, it quickly exits the nanopore via the vestibule again. If the tag remains close to the nanopore after exiting, the same process can occur repeatedly over time leading to noise on the sequencing signal. The plot in FIG. 10A shows both bright mode data 1001 and dark mode data 1002 in a case where no threading events have occurred. Thus, the entirety of the bright mode data 1001 includes only open channel signal values. However, other than in the first 125 ms, the bright mode data 1001 is subject to FCN. Like the case for PTBN, even though the system is still in the open channel state, FCN can result in signal values that are very close to or even equal to the levels that represent a valid threading event. Thus, if FCN is not removed prior to base calling, sequencing errors can result.

FIG. 10B shows a period-to-period difference signal computed from the bright mode signal data 1001. FIG. 10B clearly shows that the amplitudes of most of the points in the period-to-period difference signal are significantly higher during the time period when FCN is occurring (during the time period from approximately 0.125 s to 3.7 s). On the other hand, during a normal open channel state (during the time period from approximately 0 s to 0.125 s) the amplitudes of most of the points in the period-to-period signal is lower. Accordingly, one or more points in the sequencing signal can be identified as high probability FCN noise points by identifying the points in the period-to-period difference signal that have an amplitude above a threshold level. Once these points are identified, they can be removed from the original signal to produce a denoised signal, as described in further detail below in reference to FIGS. 11-13.

IV. De-Noising Using Difference Data

As introduced above in reference to FIGS. 10-11, in some cases, certain types of noise can exhibit a period-to-period difference signal that is significantly larger than the difference signal for a clean open channel state that is unaffected by noise. Accordingly, one or more noise points can be identified from the difference signal by identifying the points that contribute to a period-to-period signal having a value above some threshold value. Conversely all points that occur below the threshold value can be identified as true signal (open channel or threaded channel data). While many different possibilities exist for denoising a signal based on the period-to-period difference, two techniques are described below for the purposes of illustration.

A first technique uses one or more thresholds on the "raw" period-to-period difference signal. The second technique uses on an intermediate step of first denoising/smoothing the period-to-period difference signal and then identifying noise points in the denoised period-to-period signal using one or more thresholds in a manner that is identical to the first method. In the second method, any method for denoising the period-to-period difference signal can be employed, but due to the particular form of the threading event in the period-to-period signal (pairs of sharp negative and positive square peaks), denoising using Haar mother wavelets is particularly advantageous as described in further detail below.

A. De-Noising Using Thresholds on Raw Difference Data

FIG. 11 shows how a raw sequencing signal can be de-noised using a thresholding technique as applied to a raw period-to-period difference data. The top panel 1119 of FIG. 11 shows the raw sequencing signal having both bright mode data 1103 and dark mode data 1105. Also shown in the bright mode data 1103, just preceding approximately 255.9 seconds, is a threading event 1107. This threading event 1107 persists over two AC periods as can be seen by the two dips in the signal at 1107a and 1107b. Also shown in the bright mode data 1103 are several potential noise data points, e.g., potential noise points 1109 and 1111.

The bottom panel 1125 of FIG. 11 shows the resulting raw period-to-period difference signal computed from a one period shift on the raw sequencing signal shown in top panel 1119. Also shown in bottom panel 1125 are two thresholds 1113 and 1117 that are set at period-to-period difference values of +/−5.0, respectively. To denoise the raw signal, all points associated with the period-to-period difference values that are greater than +/−5.0 thresholds can be identified as noise points. According to certain embodiments, both points in the raw signal that are used to compute the period-to-period difference can then be identified as noise points. Alternatively only one of the points, e.g., the first or the second point used to compute the difference, can be identified as a noise point.

The second panel 1121 in FIG. 11 shows the set of noise points (shown as open circles) that are determined by selecting all points that result in a period-to-period difference values of greater than +/−3. It should be noted that the positive and negative peaks of the actual threading event will also get removed in this procedure but this does not necessarily eliminate all of the threaded signal from the sequencing data. As discussed above in reference to FIG. 8, most of the time, a threading event persists over many AC cycles and thus, only the data associated with the very end of the threading event and the very beginning of the threading event will be removed using the threshold technique because these are the only points that exhibit large values in the period-to-period difference signal. In the intervening region between these beginning and ending peaks, the data will fluctuate about zero but still does, in fact, correspond to useful signal because it includes threaded data points, as can be best seen in the period-to-period data shown in FIG. 8.

Advantageously, the difference data amplitude in the threaded state data that is between the positive and negative peaks is comparable to the difference data amplitude in the open channel, but is significantly smaller than the difference data amplitude in other areas that are affected by one or more noise sources, e.g., PTBN and FCN as described above in reference to FIGS. 9-10. Accordingly, the thresholding procedure applied to the difference data can discriminate between the sequencing "true" signal values (threaded and open channel points) and the false signal values that can be caused by one or more sources of noise (other large amplitude points in the difference data). Once the noise points (open circles in the second panel) are identified using the period-to-period thresholds, they can be removed from the raw signal, resulting in a denoised sequencing signal as shown in the third panel 1123 of FIG. 11. It can be seen that the denoised signal is significantly cleaner than the raw signal shown in panel 1119, but still contains a clear threaded signal 1127 located just before approximately 255.9 seconds.

While the example shown here applies only a single set thresholds, multiple sets of thresholds can be applied to remove only data point that fall within one or more ranges of thresholds. Alternatively, adaptive thresholds can be applied that use different threshold values at different times, e.g., depending on the nature of the data itself and whether or not certain noise sources are present.

As described elsewhere, e.g., in U.S. patent application Ser. No. 15/632,190 titled, "Formation and Calibration of Nanopore Sequencing Cells," U.S. Provisional Patent Application No. 62/591,099 titled, "Normalization and Baseline Shift Removal by Rotation in Added Data Dimensions," and U.S. patent application Ser. No. 15/628,353 titled, "Period-to-Period Analysis of AC Signals from Nanopore Sequencing" the disclosures of which are incorporated by reference in their entireties for all purposes, the sequencing signal (in this case the denoised sequencing signal) can be fed downstream for further processing, e.g., further filtering via Kalman filter or the like, or further processing via two-dimensional transformation, and can be analyzed in a base calling processing to identify a DNA sequence from the signal values of the denoised sequencing signal.

B. De-Noising Using Thresholds on Wavelet Denoised Difference Data

According to certain embodiments, the thresholding procedure described above can be employed on a period-to-period difference signal that itself has been previously denoised, filtered, or smoothed by some other means. Any denoising/filtering/smoothing procedure can be used to pre-preprocess the difference signal in this manner. According to certain embodiments, due to the shape of the threading events in the period-to-period difference signal, a wavelet denoising process employing a Haar mother wavelet can be used to effectively denoise the signal. FIG. 12C shows examples of the first six Haar wavelets and also illustrates that this form of wavelet closely resembles the threading events within the period-to-period difference signal (i.e., the wavelet's fundamental shape includes positive and negative square pulses, similar to a threading event in the period-to-period difference signal).

The process of wavelet denoising can include three steps. First, a multi-level discrete wavelet decomposition of the noisy signal is performed to obtain a set of wavelet detail coefficients for each level j of the decomposition. For example a 5 level decomposition would have 5 sets of detail coefficients. More specifically, a discrete wavelet decomposition can be interpreted as computing the wavelet coefficients of a discrete set of child wavelets for a given mother wavelet $\psi(t)$, where the child wavelets are generated by shifting and scaling the mother wavelet by powers of two. Accordingly, for each level j, the set of child wavelets are $$\psi_{j,k}(t) = \frac{1}{\sqrt{2^j}} \psi\left(\frac{t - k2^j}{2^j}\right) \quad (4)$$

where j is referred to as the scale or level parameter and k is the shift parameter and both are integers. Using the set of child wavelets defined by Eqn. (4), the detail coefficients $\gamma_{jk}$ (for the level j) for a signal x(t) having a length $2^N$ can be found by projecting the signal x(t) onto the set of child wavelets j fixed according to the following integral $$\gamma_{jk} = \int_{-\infty}^{\infty} x(t) \frac{1}{\sqrt{2^j}} \psi\left(\frac{t - k2^j}{2^j}\right) dt \quad (5)$$

where k ranges from 0 to $2^{N-1}$. Thus, the output of a multi-level discrete wavelet decomposition taken to level L is L sets of detail coefficients $\gamma_{1k}, \gamma_{2k}, \ldots, \gamma_{Lk}$. Stated in words, for each level j the detail coefficients are computed by taking a convolution of the noisy signal x(t) with a dilated, reflected, and normalized version of the mother wavelet sampled at the points 1, $2^j$, $2^{2j}$, ..., $2^N$. Thus, for each level, if the noisy signal includes 100,000 data points there will be 100,000 detail coefficients.

After the detail coefficients are determined, a thresholding process is applied to modify each level's set of coefficients according to some thresholding rule. The particular form for the thresholding function used in the wavelet denoising scheme can vary but the so-called "hard" and "soft" thresholding techniques are often used. Both thresholding schemes set to zero all detail coefficients that have a magnitude that is less than the threshold. However, hard and soft thresholding differ in how they process the remaining detail coefficients that have magnitudes that are greater than or equal to the threshold. In soft thresholding, the magnitude of the remaining detail coefficients are decreased by subtracting the threshold value from the detail coefficient value. In hard thresholding, the remaining detail coefficients are left unchanged.

Because the thresholded detail coefficients are eventually used as the wavelet coefficients with which to reconstruct the filtered signal, the effect of the thresholding process is to effectively increase the relative importance in the reconstructed signal of wavelet functions that closely resemble the noisy data signal, but discard or deemphasize wavelet functions that do not resemble the noisy signal at that data point.

Once the thresholded detail coefficients are computed, the denoised signal is reconstructed by the inverse wavelet transform using the thresholded coefficients. This reconstructed signal provides a filtered data signal that has less noise but still preserves the signal high frequency content.

Many wavelet based signal processing libraries include a wavelet denoising function that can simplify the multi-step denoising process by implementing a function that takes as input the noisy signal and a set of parameters, and outputs a wavelet denoised signal. One such example is the function 'wden' that is available within the Matlab scientific computing platform. The function takes several parameters as input with the function taking the form wden(X, TPTR, SORH, SCAL, N, 'wname'). X is the noisy signal TPTR is a character vector that contains the threshold selection rule (e.g., SURE thresholding, universal thresholding, minimax thresholding, etc.), SORH is a parameter that sets the type of thresholding that will be applied (soft or hard thresholding), SCAL is an option to use multiplicative threshold rescaling or not, the parameter 'N' defines the level of the multi-level discrete wavelet decomposition, and finally 'wname' is the name of the wavelet to be used for the decomposition and recomposition (e.g., the various Daubechies wavelets, Haar wavelets, Coiflets, Symlets, etc.). Other similar wavelet packages can be used such as those found within the Python "pywt" library and the like. The above are provided herein mere for the sake of illustration and any wavelet denoising process can be employed without departing from the scope of the present disclosure.

Figure 12A:
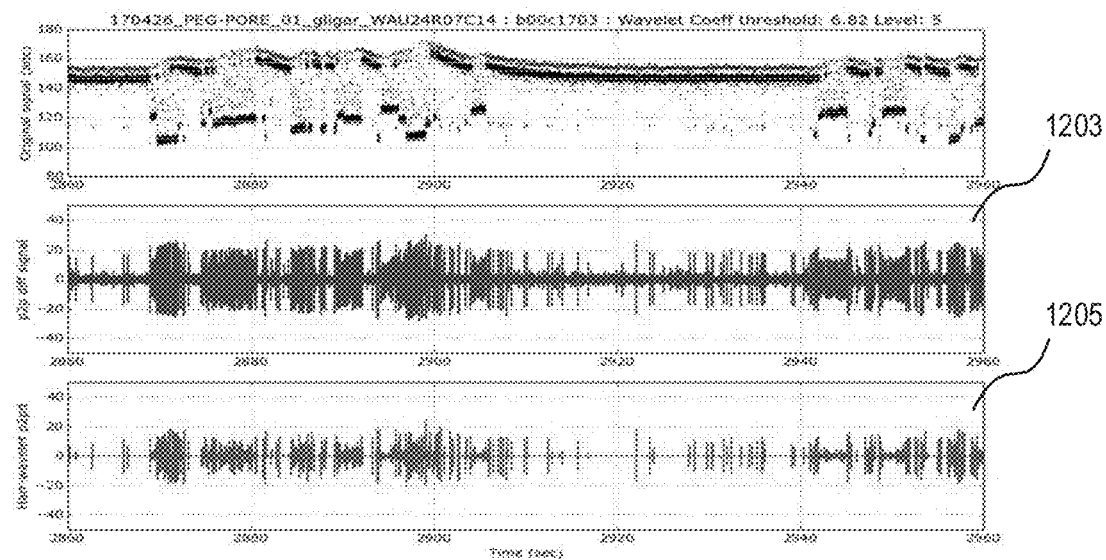
FIGS. 12A and 12B illustrate one example of a comparison between a raw period-to-period difference signal and a Haar wavelet denoised period-to-period difference signal, according to certain aspects of the present disclosure.
Figure 12B:
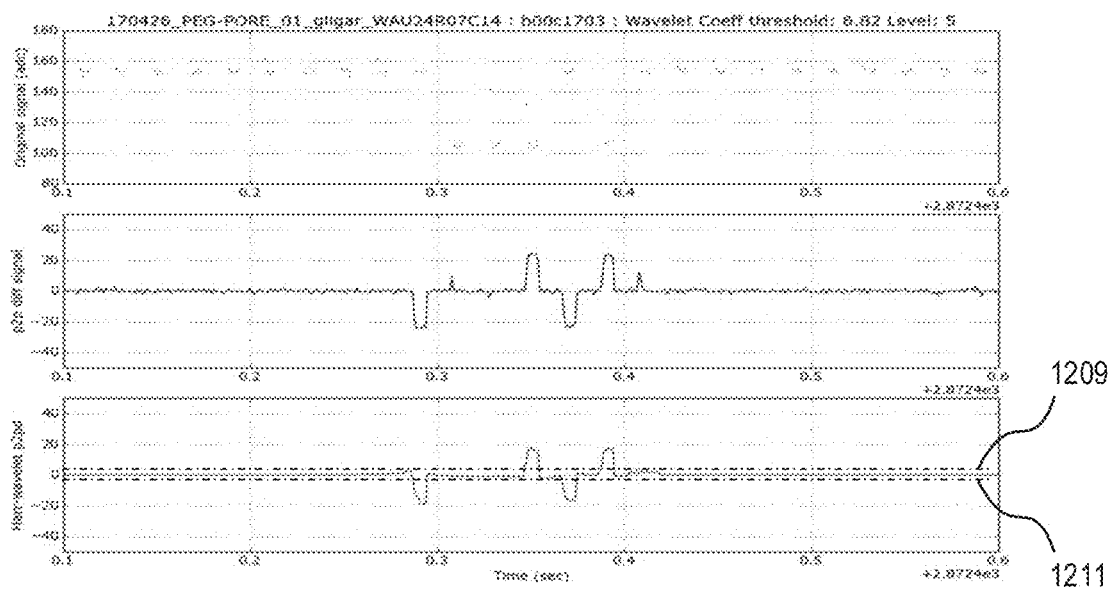
Figure 12C:
FIG. 12C shows examples of the first six Haar wavelets and also illustrates that this form of wavelet closely resembles the threading events within the period-to-period difference signal.

FIGS. 12A-12B show the results of 5 level Haar wavelet desnoising using the so-called "universal threshold" with "hard" thresholding according to certain embodiments. The so-called "universal threshold" $\lambda_L$ is defined for each level L and is given by the following:

$$\lambda_L = \sigma_L \sqrt{2 \log(n)} \quad (6)$$

where $\sigma_L$ is the standard deviation of the noise for a given level and n is the sample size.

Rather than computing the standard deviation directly, it is often useful to estimate it using the wavelet coefficients that were provided as a result of the decomposition. More specifically, for a wavelet decomposition, the standard deviation of the noise $\sigma_L$ can be estimated from the median of the absolute value of the wavelet coefficients (MAD) as follows:

$$\sigma_L = MAD_L/0.6745$$

The rationale for the use of the "universal threshold" is that it removes all wavelet coefficients that are smaller than the expected maximum of an assumed independent and identically distributed (i.i.d) normal noise sequence of sample size n and thus is optimal from a signal-to-noise perspective.

FIG. 12A shows one example of a comparison between a raw period-to-period difference signal 1203 and a Haar wavelet denoised period-to-period difference signal 1205. As can be seen from the comparison, the Haar wavelet denoising effectively removes the low amplitude portions of the raw period-to-period difference signal and keeps a nontrivial fraction of the high amplitude portions thereby providing a base period-to-period signal that can provide improved identification of noise points using the thresholding procedure described above in reference to FIG. 11. For example, as shown in FIG. 12B, after the period-to-period difference signal is itself denoised using the wavelet method, a set of noise points can be determined from that wavelet denoised period-to-period signal by applying one or more thresholds 1209 and 1211 in a manner that is identical to that described above in reference to FIG. 11.

Figure 13:
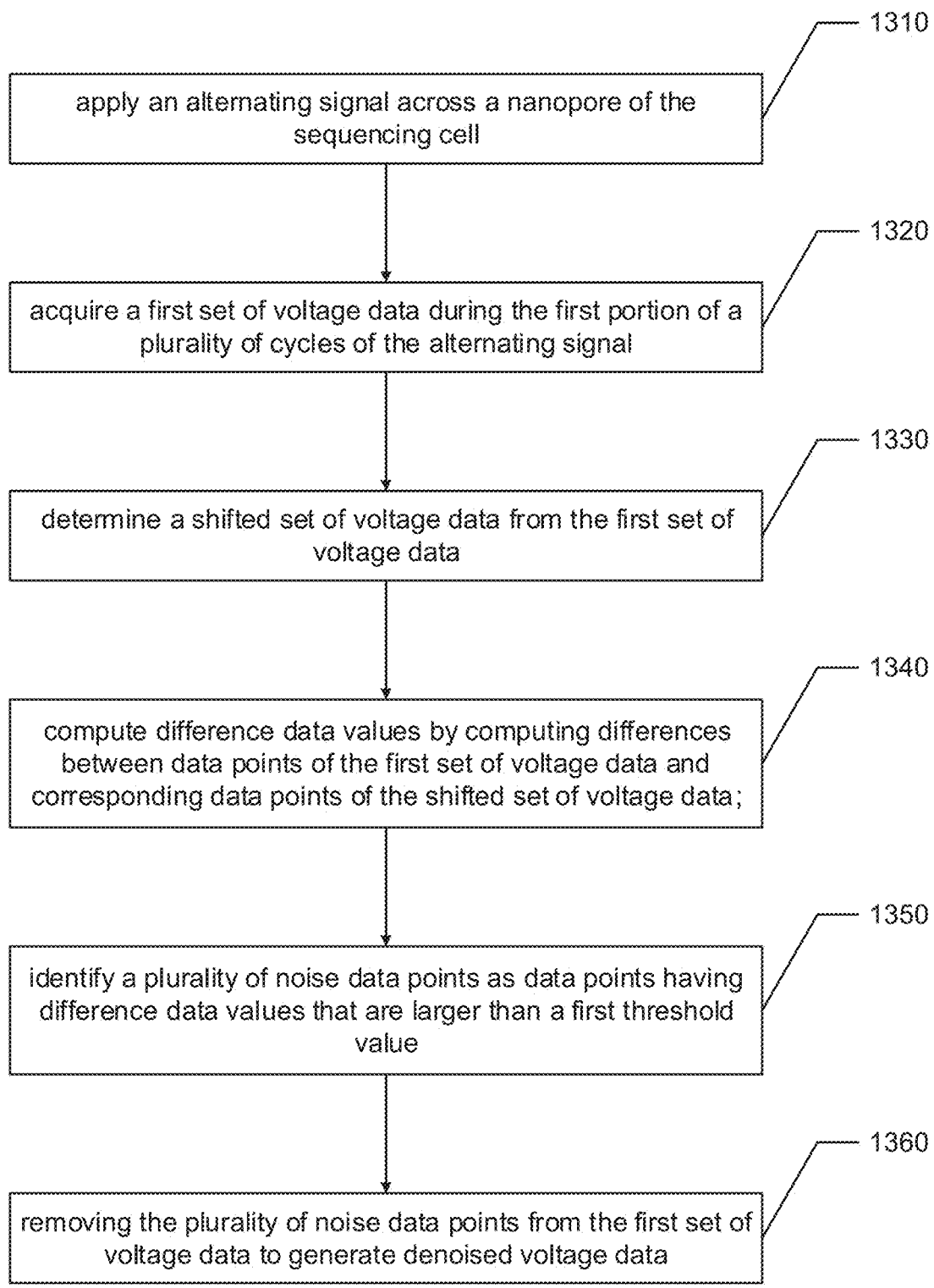
FIG. 13 is a flow chart illustrating an example method of using a sequencing cell, according to certain embodiments.

FIG. 13 is a flow chart illustrating an example method of using a sequencing cell, according to certain embodiments. More specifically, FIG. 13 illustrates a method of denoising a sequencing signal using a period-to-period analysis of AC signals from nanopore sequencing according to some embodiments.

In step 1310, an alternating signal (also referred to herein as an "AC signal") is applied across a nanopore of the sequencing cell. Such an AC signal may be a square wave provided by an AC signal generator, similar to AC voltage source 420 (also referred to herein as an AC "signal generator") described above in reference to FIG. 4. In some embodiments, the AC signal may be multiple cycles long with each cycle of the alternating signal comprising a first portion (also referred to herein as the "bright mode" or "bright period") and a second portion (also referred to herein as the "dark mode" or "dark period"). The voltage levels of the second portion are opposite of a reference voltage than a voltage levels of the first portion ($V_{LIQ}$ is either above or below $V_{PRE}$ in the embodiment shown in FIG. 5). As described above in reference to FIGS. 1-2, in some embodiments, the nanopore is configured to receive a tag that is connected to a nucleotide thereby creating a threading event.

In step 1320, a first set of voltage data (also referred to herein as "unshifted voltage data" or "raw voltage data") is acquired, e.g., by ADC 410, as described above in reference to FIG. 4. In some embodiments, the first set of voltage data is acquired during the first portion (e.g., the bright period) of the multiple cycles of the alternating signal. Examples of the first set of voltage data include the data points shown in bright period 520 of FIG. 5 and also all points characterized as within a "B" period, as shown in FIGS. 7-8. As shown in FIG. 7-8, the first set of voltage data can include voltage data points acquired over multiple cycles of the AC signal. As described above, voltage data corresponds to (i.e. depends on) a value of a resistance of the nanopore at a different time, where the resistance of the nanopore changes when the tag is received within the nanopore.

In step 1330, a time-shifted set of voltage data is determined from the acquired raw voltage data e.g., by digital processor 430 shown above in FIG. 4. Examples of shifted data are shown in FIGS. 7-8, as discussed above. In some embodiments, each cycle of data points of the raw set of voltage data and the shifted set of voltage data includes a specified number of data points, the raw unshifted data may include 15 data points within a bright period and the shifted data may include a corresponding 15 data points within a bright period. Because the shifted data is time-shifted relative to the unshifted data the data points of the shifted data and the data points of the unshifted data are from different cycles of the AC signal, as discussed above, e.g. in reference to FIGS. 7-8 above.

In step 1340, difference data is computed, e.g., by digital processor 430 shown above in FIG. 4, by computing differences between data points of the unshifted set of voltage data and corresponding data points of the shifted set of voltage data. In some examples, the corresponding data points have the same position in a respective cycle but may be present in different cycles. For example, for unshifted data points that originate from cycle 1 of the unshifted data and shifted data points originate from cycle 2 of the unshifted data, difference data may be computed in the following manner: the first difference data point may be computed by subtracting the first point from cycle 1 from the first point of cycle two, the second difference data point may be computed by subtracting the second point from cycle 1 from the second point of cycle 2, and so on. One of ordinary skill having the benefit of this disclosure will appreciate that there are many different ways to perform the difference, and the single point method described above is meant as merely one example among many. For example, multiple data points from each cycle may be averaged or filtered before subtraction or differences may be computed based on nearest neighbor subtractions, next nearest neighbor subtractions or the like without departing form the scope of the present disclosure.

Optionally, the difference data can be further processed, e.g., by filtering, smoothing, and/or denoising. As described above, once the difference data is computed in step 1340, a wavelet denoising technique can be used to generate denoised difference data. This denoised difference data can be fed to step 1350 below but, also optionally, the denoised difference signal can be inverted to recover a corresponding filtered, smoothed, or denoised set of voltage data without needing to apply additional thresholds to the data as described below in reference to step 1350. To recompute the denoised set of voltage data from the denoised difference data it may be necessary to use a sum signal between the original voltage data and the time shifted voltage data. For example, if A is the original voltage data and B is the time shifted voltage data then the sum signal S can be written as $$S = \frac{A+B}{2} \quad (7)$$

and the difference signal D can be written as $$D = \frac{A-B}{2}, \quad (8)$$

then A or B can be recovered by computing S+D or S−D, respectively. Accordingly, in some embodiments both the sum and difference signals can be stored in memory and later used to reconstruct a denoised set of voltage data from the denoised difference data.

In step 1350, a plurality of noise points are identified (either using the raw difference data or using the denoised difference data). The identification can be accomplished by a digital processor, e.g., by digital processor 430, that is programmed to identify the set of difference data points that are larger than one or more threshold values. For example, in FIG. 11, panel 1121 shows a set of identified noise points as open circles. These noise points were determined to be the data points associated with the difference data points that were larger than +/−5.

In step 1360, denoised voltage data is generated by removing the noise points are from the first set of voltage data. For example, in a case where a difference data point that is greater than 5 is computed from the difference of 10th and 20th voltage data points, both the 10th and the 20th data points can be removed in the final denoised data. Alternatively, only the 10th or the 20th point can be removed.

According to certain embodiments, the denoised data can be used for a number of different purposes. For example, the data can be further processed to remove baseline shift and/or gain drift and can be normalized and then used for base calling as described in U.S. patent application Ser. No. 15/632,190, U.S. Provisional Patent Application No. 62/591,099, and U.S. patent application Ser. No. 15/669,207, which are incorporated by reference in their entirety for all purposes. In some embodiments, one or more threading events can be identified by the signal processing system using one or more data points in the denoised data and based on their levels the system can determine the nucleotide(s) that were incorporated into a nucleic acid in the sequencing cell.

In addition, the denoised data can be used to compute another cycle of period-to-period difference signals. In this case, a data imputation process where the noise data that has been removed is replaced with one or more substitute values before the second period-to-period difference is computed. For example, the missing data can be replaced with an interpolated value that is midway between the two adjacent values or the missing data can be replaced with a zeros. As would be appreciated by one of ordinary skill in the art with the benefit of this disclosure many different data imputation methods can be employed. In some cases, the imputation method may be chosen to not significantly shift and of the peak values in the sequencing signal histogram used for base calling.

V. Results

FIGS. 14A-16D show sample data using the denoising technique described herein. More specifically FIGS. 14A-16D show how a sequencing signal can be denoised by determining noise points using thresholds on the raw period-to-period difference data (the preprocessing step of wavelet denoising in not employed in this example.)

Figure 14A:
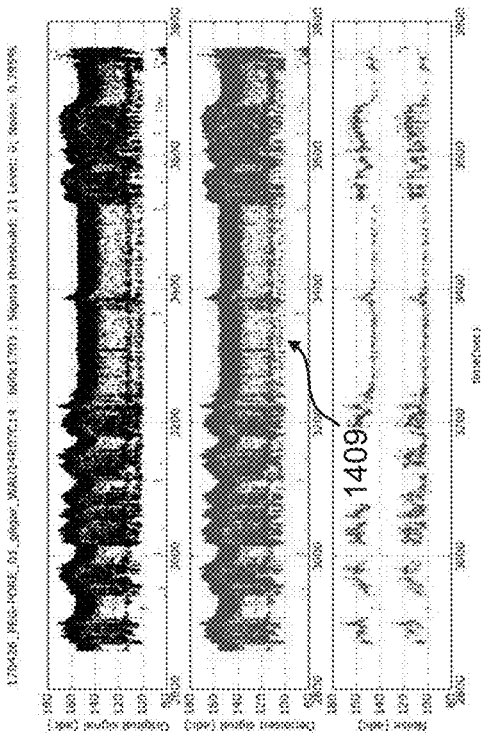
FIGS. 14A-14D illustrate sample data processed using the denoising technique, according to certain aspects of the present disclosure.

Each figure shows a set of three different plots. The top plot shows the raw sequencing signal, the middle plot shows the denoised signal, and the bottom plot shows the noise points that were removed because these points had a larger period-to-period difference signal than the threshold. FIG. 14A starts with the largest threshold value and the threshold value decreases with each subsequent figure. Each figure starts with the same set of signal values and the only difference from plot to plot is the change in the choice of threshold value for determining the noise points from the period-to-period difference signal.

FIG. 14A shows the effect of denoising using a relatively large threshold of +/−31 ADC counts. As can be inferred from the bottom plot of FIG. 14, very few points have period-to-period differences that are larger than 31. Only noise points 1401 appearing near t=3.75 s are removed representing only 0.006% of the total data. Accordingly it can be assumed that a threshold of 31 is too high to effectively denoise the signal.

Figure 14C:
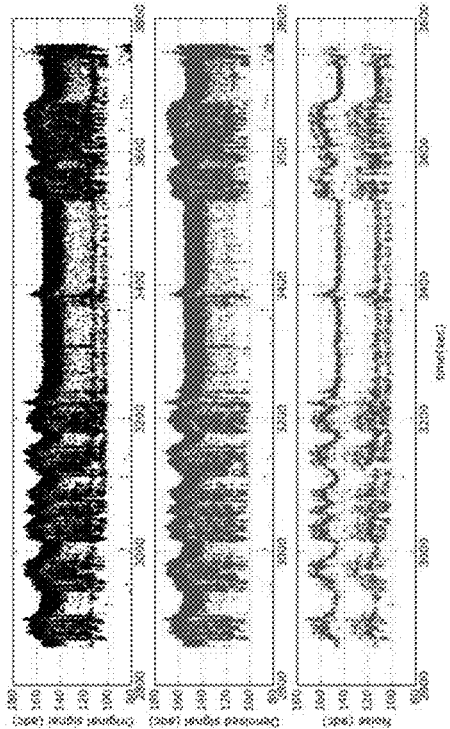
Figure 14B:
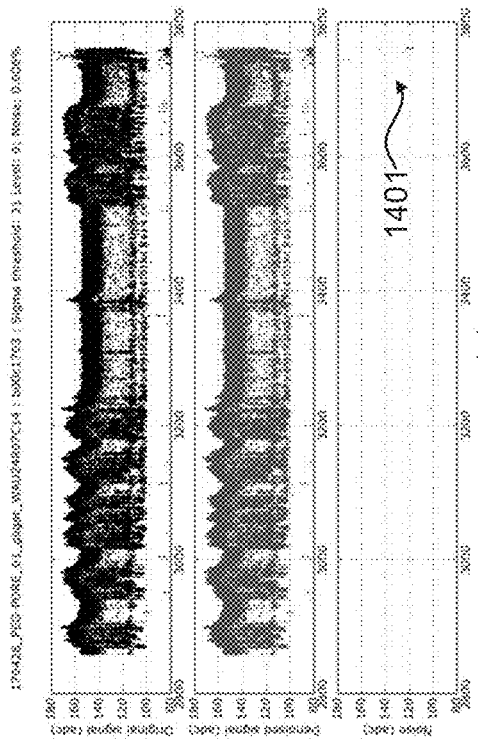

FIG. 14B shows the effect of denoising using a slightly lower threshold of +/−25 ADC counts. As can be seen from the bottom plot of FIG. 14B, two distinct groups of noise points. Advantageously these noise points are not randomly distributed in ADC counts, but rather group 1403 is centered just below an ADC value of approximately 160 and group 1405 is centered just above 100 ADC counts. These data points are clustered about these two ADC values because they are caused by a common noise source: PTBN. A portion of the PTBM noise signal can be seen in the top plot of each figure as faint lines of points, e.g., lines 1407, running through what appears to be the entire length of the acquisition. The number of noise data points shown in the bottom plot of FIG. 14B, and that are removed from the denoised signal shown in the middle plot, represent only 0.197% of the total data.

FIG. 14C shows the effect of denoising using a slightly lower threshold of +/−21 ADC counts. As can be seen from the bottom plot of FIG. 14C, the two distinct groups of noise points that were present in FIG. 14B are still present and appear to possess even more points. The number of noise data points shown in the bottom plot of FIG. 14C, and that are removed from the denoised signal shown in the middle plot, represent only 0.795% of the total data. This threshold value appears to still not be low enough to completely remove the PTBN as the PTBN clusters 1409 are still visible in the middle plot showing the denoised data.

Figure 14D:
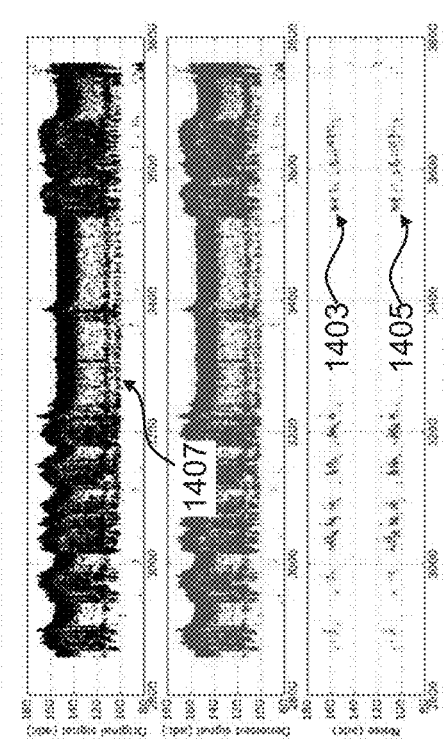
Figure 15A:
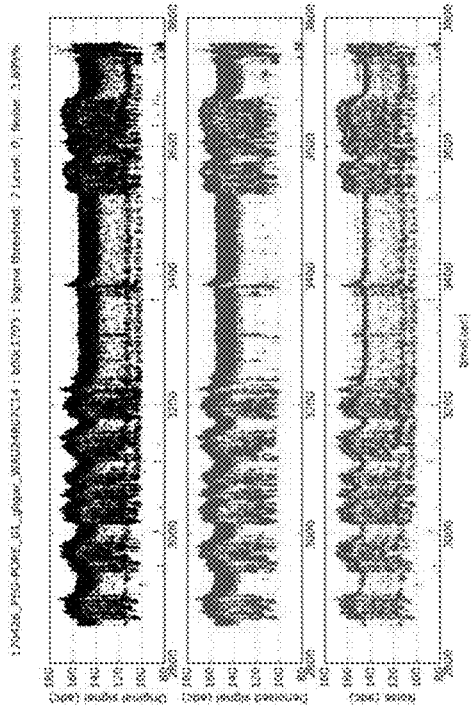
FIGS. 15A-15D illustrate sample data processed using the denoising technique, according to certain aspects of the present disclosure.
Figure 15B:
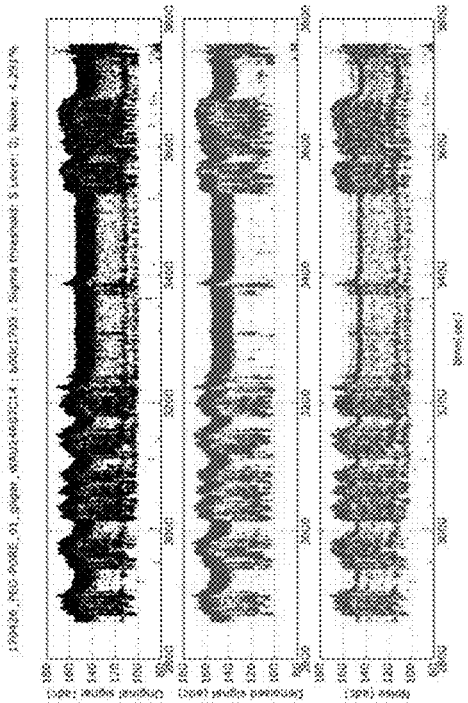
Figure 15C:
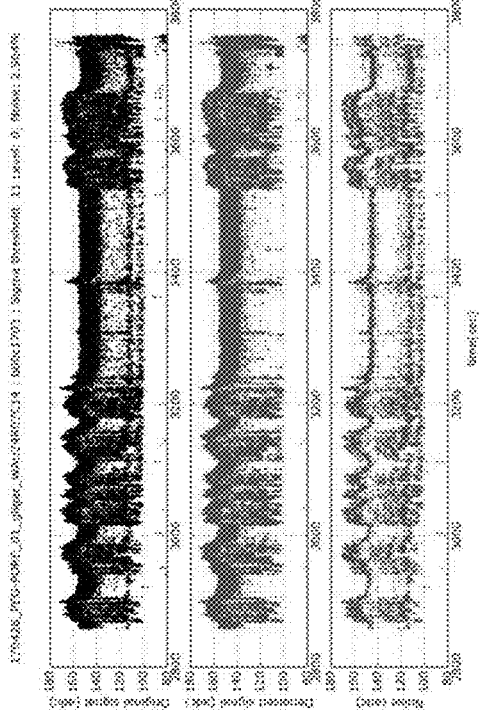
Figure 15D:
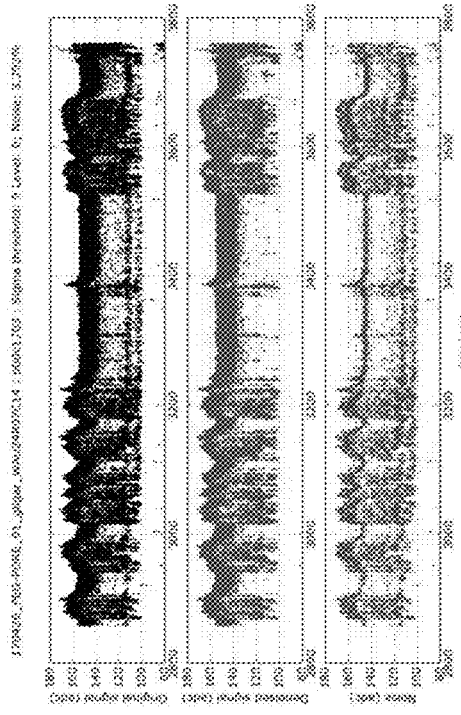
Figure 16A:
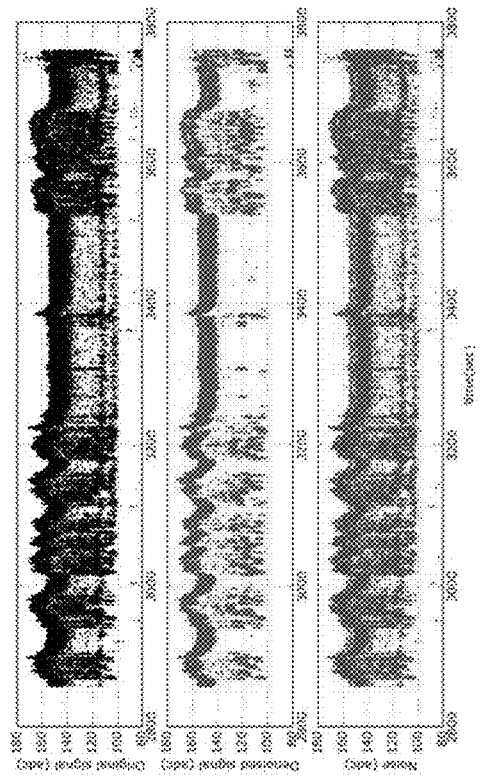
FIGS. 16A-16D illustrate sample data processed using the denoising technique, according to certain aspects of the present disclosure.
Figure 16B:
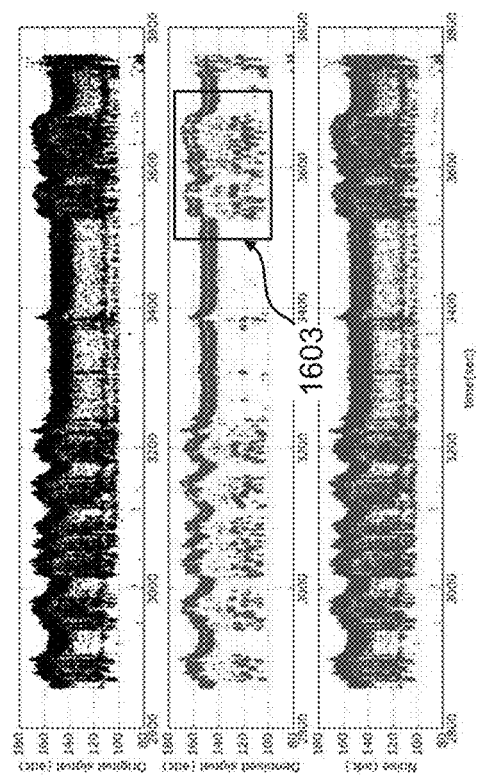
Figure 16C:
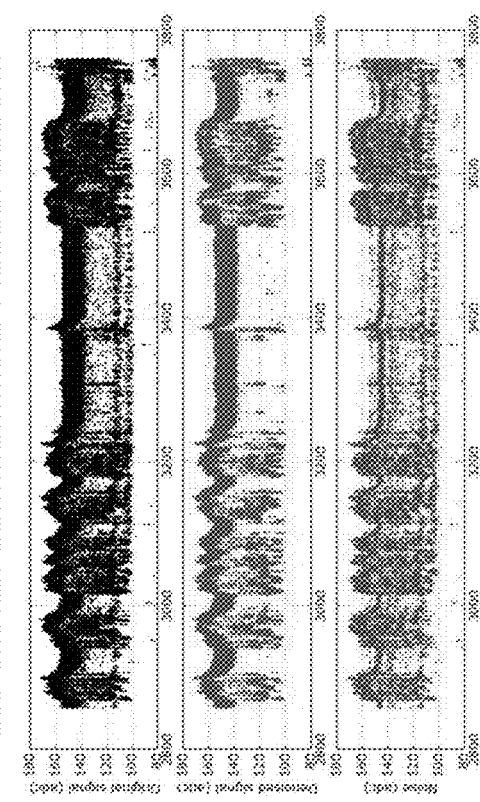
Figure 16D:
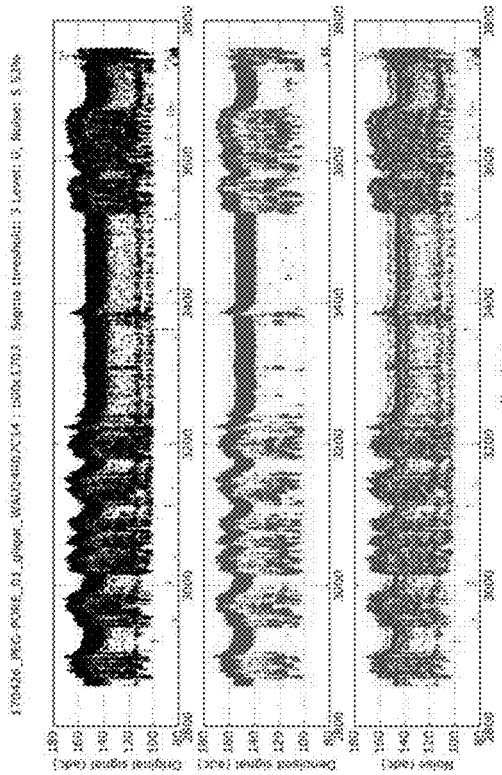

FIG. 14D shows the effect of denoising using an even lower threshold of +/−15 ADC counts. The number of noise data points shown in the bottom plot of FIG. 14C, and that are removed from the denoised signal shown in the middle plot, now represent only 2.263% of the total data. In this case, the PTBN clusters appear to be completely removed from the denoised signal shown in the middle plot of FIG. 14D.

FIGS. 15A-15D show the effect of progressively lower threshold values of +/−11, +/−9, +/−7, and +/−5, which remove 2.964%, 3.292%, 3.695% and 4.291% of the data respectively. Even at the relatively low threshold of +/−7, the de noising appears to not have degraded the open channel or threaded channel data, even in the denoised signal.

FIGS. 16A-16D show the effect of progressively lower threshold values of +/−4, +/−3, +/−2, and +/−1, which remove 4.735%, 5.53%, 9.792% and 38.722% of the data, respectively. Remarkably, a threshold of only 2 still preserves approximately 90% of the data implying that 90% of the difference data point have values that are less than or equal to 2. Not until the threshold is set to the minimum value of 1 does the method start to remove significant amounts of data and even then, the data shown in FIG. 16D proves that for this example over 60% of the difference data has a value of +/−1 and 0 (the only possible ADC points for such a low threshold). Such a finding implies that this technique can be used effectively remove the noise points without dramatically affecting the open channel and threaded channel data. In fact, even for the +/−1 case shown in FIG. 16D, the middle plot showing the cleaned signal appears to have a relatively noise free sequencing signal, with clusters of threading events, e.g., cluster 1603 clearly visible below the open channel baseline.

VI. Computer System

Any of the computer systems mentioned herein may utilize any suitable number of subsystems. Examples of such subsystems are shown in FIG. 17 in computer system 1710.

In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

Figure 17:
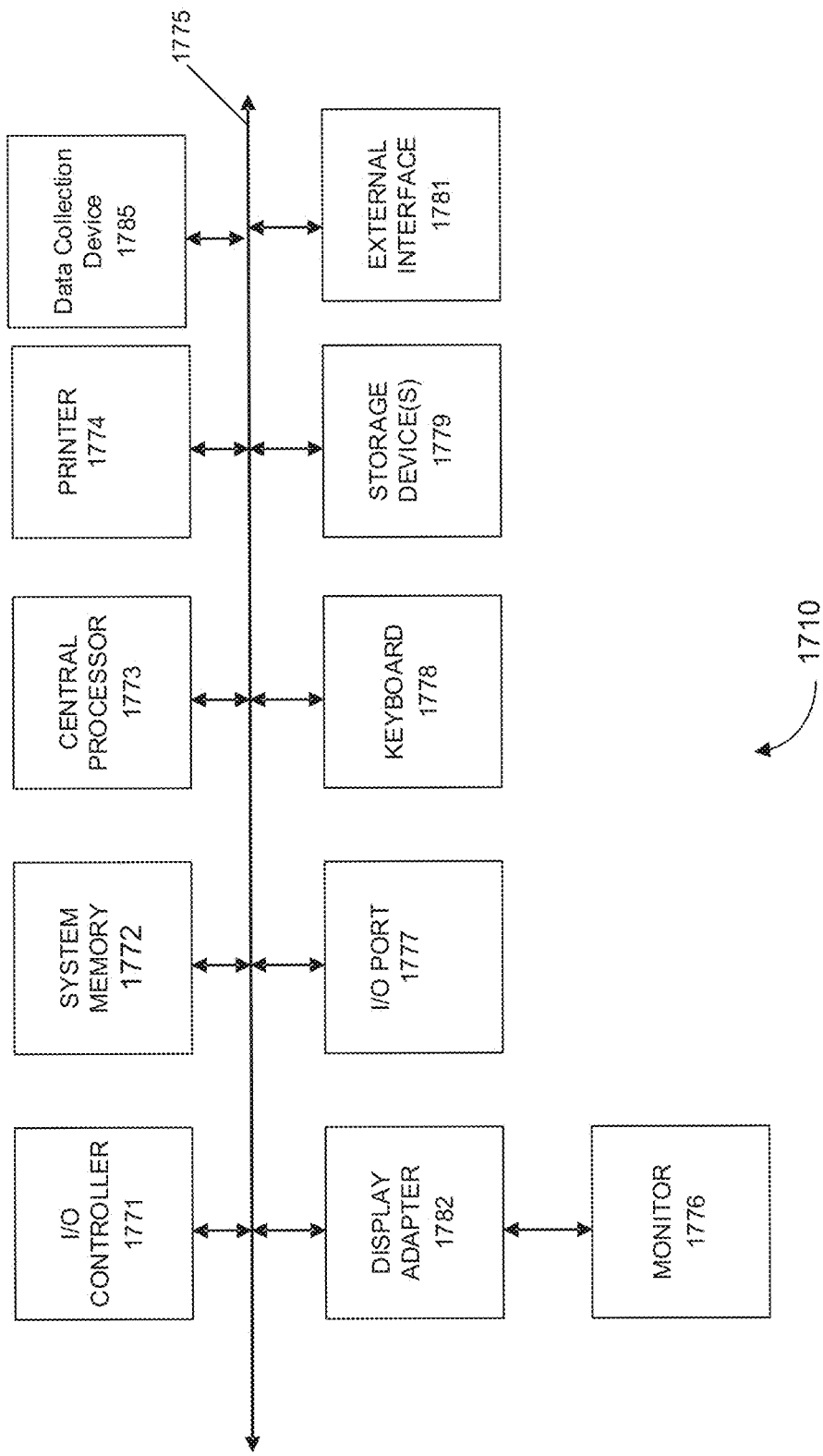
FIG. 17 illustrates a computer system, according to certain aspects of the present disclosure.

The subsystems shown in FIG. 17 are interconnected via a system bus 1775. Additional subsystems such as a printer 1774, keyboard 1778, storage device(s) 1779, monitor 1776, which is coupled to display adapter 1782, and others are shown. Peripherals and input/output (I/O) devices, which couple to I/O controller 1771, can be connected to the computer system by any number of means known in the art such as input/output (I/O) port 1777 (e.g., USB, FireWire®). For example, I/O port 1777 or external interface 81 (e.g. Ethernet, Wi-Fi, etc.) can be used to connect computer system 1710 to a wide area network such as the Internet, a mouse input device, or a scanner. The interconnection via system bus 1775 allows the central processor 1773 to communicate with each subsystem and to control the execution of a plurality of instructions from system memory 1772 or the storage device(s) 1779 (e.g., a fixed disk, such as a hard drive, or optical disk), as well as the exchange of information between subsystems. The system memory 1772 and/or the storage device(s) 1779 may embody a computer readable medium. Another subsystem is a data collection device 1785, such as a camera, microphone, accelerometer, and the like. Any of the data mentioned herein can be output from one component to another component and can be output to the user.

A computer system can include a plurality of the same components or subsystems, e.g., connected together by external interface 1781 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

The invention claimed is:

1. A system or instrument, comprising:
   a sequencing cell that includes a nanopore, the nanopore configured to receive a tag that is connected to a nucleotide, thereby creating a threading event;
   a signal generator configured to apply an alternating signal across the nanopore of the sequencing cell, each cycle of the alternating signal comprising a first portion and a second portion, wherein the first portion is set at a first voltage level and the second portion is set at a second voltage level and a reference voltage is set in between the first voltage level and the second voltage level;
   an analog-to-digital converter configured to acquire a first set of voltage data during the first portion of a plurality of cycles of the alternating signal, wherein each data point of the first set of voltage data corresponds to a value of a resistance of the nanopore at a different time, where the resistance of the nanopore is configured to change when the tag is received within the nanopore; and one or more processors configured to execute instructions stored on a computer readable medium to:

determine a period shifted set of voltage data from the first set of voltage data, wherein each cycle of data points of the first set of voltage data and of the period shifted set of voltage data includes a specified number of data points;

compute difference data values by computing differences between data points of the first set of voltage data and corresponding data points of the period shifted set of voltage data;

identify a plurality of noise data points as data points having difference data values with magnitudes that are larger than a first threshold value;

determine a denoised first set of voltage data by removing the plurality of noise data points from the first set of voltage data; and using the denoised first set of voltage data to determine an identity of the nucleotide.

2. A method of using a sequencing cell, the method comprising:

applying an alternating signal across a nanopore of the sequencing cell, the nanopore configured to receive a tag that is connected to a nucleotide, thereby creating a threading event, each cycle of the alternating signal comprising a first portion and a second portion, wherein the first portion is set at a first voltage level and the second portion is set at a second voltage level and a reference voltage is set in between the first voltage level and the second voltage level;

acquiring a first set of voltage data during the first portion of a plurality of cycles of the alternating signal, wherein each data point of the first set of voltage data corresponds to a value of a resistance of the nanopore at a different time, where the resistance of the nanopore changes when the tag is received within the nanopore;

determining a period shifted set of voltage data from the first set of voltage data, wherein each cycle of data points of the first set of voltage data and of the period shifted set of voltage data includes a specified number of data points;

computing difference data values by computing differences between data points of the first set of voltage data and corresponding data points of the period shifted set of voltage data;

identifying a plurality of noise data points as data points having difference data values with magnitudes that are larger than a first threshold value; and determining a denoised first set of voltage data by removing the plurality of noise data points from the first set of voltage data;

identifying the threading event using one or more data points in the denoised first set of voltage data;

determining a level of the threading event; and using the level to determine an identity of the nucleotide.

3. The method of claim 2, wherein identifying the plurality of noise data points further includes identifying data points having difference data values that are less than a second threshold value.

4. The method of claim 2, further comprising filtering the difference data before identifying the plurality of noise data points.

5. The method of claim 4, wherein filtering the difference data includes computing wavelet denoised difference data.

6. The method of claim 5, wherein a wavelet used for filtering the difference data is a Haar wavelet.

7. The method of claim 6, wherein identifying the plurality of noise data points includes identifying the plurality of noise data points as data points having wavelet denoised difference data values that are larger than the first threshold value.

8. A system or instrument, comprising:

a sequencing chip that includes a plurality of sequencing cells, wherein a first sequencing cell includes a nanopore, the nanopore configured to receive a tag that is connected to a nucleotide of a nucleic acid, thereby creating a threading event;

a signal generator configured to apply an alternating signal across the nanopore of the first sequencing cell, each cycle of the alternating signal comprising a first portion and a second portion, wherein the first portion is set at a first voltage level and the second portion is set at a second voltage level and a reference voltage is set in between the first voltage level and the second voltage level;

an analog-to-digital converter configured to acquire a first set of signal value data during the first portion of a plurality of cycles of the alternating signal, wherein each data point of the first set of signal value data corresponds to a value of a resistance of the nanopore at a different time, where the resistance of the nanopore is configured to change when the tag is received within the nanopore; and one or more processors configured to execute instructions stored on a computer readable medium to:

determine a period shifted set of signal value data from the first set of signal value data, wherein each cycle of data points of the first set of signal value data and of the period shifted set of signal value data includes a specified number of data points;

compute difference data values by computing differences between data points of the first set of signal value data and corresponding data points of the period shifted set of signal value data;

identify a plurality of noise data points as data points having difference data values with magnitudes that are larger than a first threshold value;

determine a denoised first set of signal value data by removing the plurality of noise data points from the first set of signal value data; and identify the threading event using one or more data points in the denoised first set of signal value data;

determine a level of the threading event; and use the level to determine an identity of the nucleotide.

9. The system or instrument of claim 8, wherein the one or more processors are further configured to identify data points having difference data values that are less than a second threshold value.

10. The system or instrument of claim 8, wherein the one or more processors are further configured to filter the difference data before identifying the plurality of noise data points.

11. The system or instrument of claim 10, wherein the one or more processors are further configured to compute wavelet denoised difference data when filtering the difference data.

12. The system or instrument of claim 11, wherein a wavelet used for filtering the difference data is a Haar wavelet.

13. The system of claim 11, wherein the one or more processors are further configured to identify the plurality of noise data points as data points having wavelet denoised difference data values that are larger than the first threshold value.

* * * * *